(12) United States Patent
Marushima et al.

(10) Patent No.: US 11,932,880 B2
(45) Date of Patent: *Mar. 19, 2024

(54) ENZYME AND METHOD FOR ASSAYING PENTOSIDINE USING SAME

(71) Applicant: Kikkoman Corporation, Noda (JP)

(72) Inventors: Kazuya Marushima, Helios (SG); Yuka Saito, Helios (SG); Yuki Tsukada, Helios (SG); Takuya Sato, Helios (SG); Yasuko Araki, Chiba (JP); Atsushi Ichiyanagi, Chiba (JP)

(73) Assignee: Kikkoman Corporation, Chiba (JP)

( * ) Notice: Subject to any disclaimer, the term of this patent is extended or adjusted under 35 U.S.C. 154(b) by 447 days.

This patent is subject to a terminal disclaimer.

(21) Appl. No.: 16/975,681

(22) PCT Filed: Feb. 27, 2019

(86) PCT No.: PCT/JP2019/007662
§ 371 (c)(1),
(2) Date: Aug. 25, 2020

(87) PCT Pub. No.: WO2019/168062
PCT Pub. Date: Sep. 6, 2019

(65) Prior Publication Data
US 2020/0407699 A1 Dec. 31, 2020

(30) Foreign Application Priority Data

Feb. 27, 2018 (JP) .................. 2018-033751

(51) Int. Cl.
*C12Q 1/26* (2006.01)
*C12N 9/04* (2006.01)

(52) U.S. Cl.
CPC ............ *C12N 9/0006* (2013.01); *C12Q 1/26* (2013.01); *C12Y 101/03* (2013.01)

(58) Field of Classification Search
CPC ....... C12N 9/0006; C12Q 1/26; C12Y 101/03
See application file for complete search history.

(56) References Cited

U.S. PATENT DOCUMENTS

| 5,370,990 A | 12/1994 | Staniford |
| 2009/0011508 A1 | 1/2009 | Takahashi |
| 2011/0028470 A1 | 2/2011 | Itokawa et al. |
| 2020/0407699 A1 | 12/2020 | Marushima |

FOREIGN PATENT DOCUMENTS

| JP | H05192193 | 8/1993 |
| JP | H08289781 | 11/1996 |
| JP | H11127895 | 5/1999 |
| JP | 2001021559 | 1/2001 |
| JP | 2007222055 | 9/2007 |
| JP | 2011239681 | 12/2011 |
| JP | 2013212109 | 10/2013 |
| JP | 2014118406 A | * 6/2014 |
| JP | 5738346 B2 | 6/2015 |
| JP | 2018068292 | 5/2018 |
| WO | 20968062 | 9/2019 |
| WO | 2019168062 | 9/2019 |

OTHER PUBLICATIONS

English Machine Translation of Japanese Application JP 2014118406 A published on Jun. 30, 2014, obtained from Espacenet on Oct. 26, 2022 (https://worldwide.espacenet.com/ (Year: 2014).*
International Search Report and Written Opinion dated May 7, 2019 in connection with PCT/JP2019/007662.
Amano et al., Recombinant expression, molecular characterization and crystal structure of antitumor enzyme, L-lysine α-oxidase from Trichoderma viride. J Biochem. Jun. 2015;157(6):549-59. doi: 10.1093/jb/mvv012. Epub Feb. 3, 2015.
Raibekas et al., Primary structure of the snake venom L-amino acid oxidase shows high homology with the mouse B cell interleukin 4-induced Fig1 protein. Biochem Biophys Res Commun. Jul. 30, 1998;248(3):476-8. doi: 10.1006/bbrc.1998.9024.
International Search Report received in PCT/JP2019/007662, dated May 7, 2019.
Written Opinion received in PCT/JP2019/007662, dated May 7, 2019.
Amano et al., "Recombinant expression, molecular characterization and crystal structure of antitumor enzyme, L-lysine-oxidase from Trichoderma viride", Jun. 1, 2015, pp. 549-559, vol. 157, No. 6, Publisher: J Biochem.
Raibekas & Massey, "Primary structure of the snake venom L-amino acid oxidase shows high homology with the mouse B cell interleukin 4-induced Fig1 protein", Jul. 30, 1998, pp. 476-478, vol. 248, No. 3, Publisher: Biochem Biophys Res Commun.
"A0A0G4DCU0 (A0A0G4DCU0_HYPRU): L-Lysine alpha-oxidase Hypocrea rufa (Trichoderma viride)", Sep. 16, 2015, Publisher: UniProtKB.
"O93364 (Oxla_Croad): L-amino-acid oxidase *Crotalus adamanteus* (Eastern diamondback rattlesnake)", Jul. 15, 1999, Publisher: UniProtKB.
PCT/JP2019/007662, May 7, 2019, International Search Report and Written Opinion.
International Search Report received in PCT/JP2020/031553, dated Oct. 27, 2020.
Written Opinion received in PCT/JP2020/031553, dated Oct. 27, 2020.

* cited by examiner

*Primary Examiner* — Louise W Humphrey
*Assistant Examiner* — Deepa Mishra
(74) *Attorney, Agent, or Firm* — Suzannah K. Sundby, Esq.; Canady + Lortz LLP

(57) ABSTRACT

The present invention provides a protein having pentosidine oxidase activity, a method for measuring pentosidine comprising: contacting the protein with a specimen; and detecting a change caused by the contact, and the like.

8 Claims, 11 Drawing Sheets

Specification includes a Sequence Listing.

SEQ ID NO: 1 g4462_DNA sequence (containing introns)

ATGAAGTCTCCCAGTCTGGCCGTGGCCGGCCTTCTTCTTGGCTCGAGTTCCTTAAGCCATGCTACCCAGCTTCGTATTGA
GACGAGGAAATCGCTCAACTCTCGTATCGCCAACGTCCACATTGATGTTGACGCTCCAGTCGCTCACCAAGTTGTCTTCA
CATATGGCCCTTGTGATTCGGAGAGCCAAGAGAACGCTCACCATGTCATTGCTCAAAGCCAAAAGCTAGAGGGCAGGAAA
CCCCATCGATTGATCTGGACTATGCCCAAGGATCTTCACCCGGATGACTGCATCTCTGCGTGGGGTGAATCAGGAGACCT
CCTCGGTCGCAGTGTCCCTCAAAAGGTCGCGCACAAGGAGATGAGGAGACGCAAGAGAGATGATAGCGACTACTCCATCC
CTATGAACAGCTCGAGTGGCATCGACGTTTATGGCCCTTGGTTCGATGGTGTAGCTCTCCCTCGAGAAGAGCGACAATCAC
AATGTGGACGTCGAAGCCGCCAAGGCCAAGGAGATTGCTATCGTCGGGGCTGGGATGGCTGGTCTGACCACGTACTTCAT
CCTCAGTGAAGCTGGACTCAGCAACCTGACGATCCTGGAGGCAAGTGGTCGTCTTGGAGGCCGCGTACGCACCGAATATC
TCTCCGGAGGACCCAGGGACCCATTCCTATGCCGAGATGGGCCCTATGCGGATCCCATACCAGGCTCGTTTTGGAGACAAG
GCATACAACATCTCGGATCAAGCAATATTCTTCCGACTTGTGGAGAAGGTGAACGAGCGGAACAAGAAGCTTGGAAACAC
CAAGGACCTCATCAACCTGATCCCGTTCATCCAGTCCAGTCCGAATGGGCTCGCTTATTATCAAGGTAACAAGCTGGAGA
ATGGGCTGCCGCCAACGCAGGCAGATGTTGCTGCAGATCCAGCACTGGGGAATGAATCCCCTGAGATCCCTGAATCTGCA
CAAGAATTGGCTGCTCAGCTTCAGAGAGCATTGCCTAACGCTGAATTCCTTGAGCTAATGGCCACAAACTTCTGGCAAGC
CCATGCCGAATTCCTCG<mark>GTAGGTGGCTCAGCCGCCCCAAGGTATAGCCAGGGCTTCAAGCGCTAGCAGTGCA</mark>
<mark>GGAATGGAATGGGGATGTAG</mark>AGAATCAGGGTCCAGCTGGCCTGCCTGGCGATCAGTGGTCTGAGTTTGCTTTCCTGGT
GAACTACCTCAACGCGACCGTCTTCGATGCCAACGCAGTCACTGGTGGTTATGACTGGCACAGCAGCCTTGACAGG<mark>GTAC</mark>
<mark>GTGACGTTGAAGAGATCTGCTGGTTCATCATTAATTCAACAGGCTGCCAGTGTACTACACTATGCTCTTGGAGCC</mark>
<mark>GGGCAGTTTCAAGACGATTGATGAGGCAAGTCAAATGACGCTTCCGGCACCTGGACGAGAACTGACAG</mark>AGCTCGC
TCGTAGGCATGAACTTGCTCCCCAACGCTTTCCATCCCCTAGTTGACGATATCACGAAGTTCAATGCAAAAGTAGAGAAG
GTTCAGCTCGATGAGAAGACTTCCCGCCTGAAGCTGCATTGGCGCGCGAACTACACTGATCCGGAGCTCGAGTCGCAGTC
ATTTGACTACGCCATTCTGTCACCTACCATGCCAGCAGTACAGAAGTTGCGCCTTCCAG<mark>GTAAGTTGCGCCATCT</mark>
<mark>GTATGTACACATTTCGTAATTTACAG</mark>GTCTACCCTTCGCTATGCGCAACGCCGTCGACTCCATGCCTTACGC
CTCTGCGTGCAAAGTCGCCCTCGAATACCGCACTCGGTTCTGGGAAAAGTTCGACAACCCCATCTACGGCTCCTGTTCCA
CCAGCACCGACATTCCCGGTATTGGATCCGTGTGCTACCCATCTTCCAACATCAACGGCAGCGGCCCAGCTTCCCTCCTT
GCGAGCTACGAGATTGGCAGGCCTTACGGCGCAGAGTGGGCTGGCATTCCTGAGGAGCAGCATGTGCAGTATGTGATTGA
CGCAATGATTGATATCCACGGCGAGGTTGCACGACGAGAGTTTACCGGGAAATGCAAGAGAAAGTGTTGGGCTCTGGACG
AGTTCTCAAACGGGGGTTGGGCTTCACCGACCGTGGGTAATCATGAGACGTATCTGCCATCGTTTTCGAGACCCACAGC
CAT<mark>GTCACTGTCCCCATTGACCTCCCTCCCAAACCTCCCCTTCCTTACCCGTTCCAG</mark>ATGATATTCGTGGGT
GAGCATACCTCCTATACACACGCATGGATCGCCTCTGCGATCGAATCTGCAGTCCGAGGCAGCGTGCAGCTGCTCTTGG<mark>G</mark>
<mark>ATGTTTCGTTTTAAATCGATGTGGCATACTCGAACAG</mark>AGCTTGGCCTTATAGACGAGGCG
AAGGATGTCGTAAACACGTGGATGGCACGATGGATCAGTGTTGTAAGTGACCTAAGCAAAGCCGTGGTGTCTGGAGCGTC
AGCGTAG (NOTE: Intronic regions are highlighted in yellow)

SEQ ID NO: 2 g4462_Putative amino acid sequence

MKSPSLAVAGLLLGSSSLSHATQLRIETPKSLNSPIANVHIDVDAPVAHQVVFTYGFCDSESQENAHRVIAQSQKLEGRK
PHRLIWTMPKDLHPDDCISAWGESGDLLGRSVPQKVAHKEMRRRKPDDSDYSIPMNSSSGIDVYGPWFIGVALLEKSDNH
NVDVEAAKAKEIAIVGAGMAGLTTYFILSEAGLSNLTILEASGRLGGRVRTEYLSGGPRDHSYAEMGPMRIPYQARFGDK
AYNISDQAIFFRLVEKVNERNKKLGNTKDLINLIPFIQSSPNGLAYYQGNKLENGLPPTQADVAADPALGNESPEIPESA
QELAAQLQRALPNAEFLELMATNFWQAHAEFLENQGPAGLPGDQWSEFAFLVNYLNATVFDANAVTGGYDWHSSLDRSSL
VGMNLLPNAFHPLVDDITKFNAKVEKVQLDEKTSRLKLHWRANYTDPELESQSFDYAILSPTMPAVQKLRLPGLPFAMRN
AVDSMPYASACKVALEYRTRFWEKFDNPIYGSCSTSTDIPGIGSVCYPSSNINGSGPASLLASYEIGRPYGAEWAGIPEE
QHVQYVIDAMIDIHGEVARREFTGKCKPKCWALDEFSNGGWASPTVGNHETYLPSFFETHSHMIFVGEHTSYTHAWIASA
IESAVRGSVQLLLELGLIDEAKDVVNTWMARWISVVSDLSKAVVSGASA

FIG. 6A

SEQ ID NO: 3 g10122_ DNA sequence (containing introns)
ATGTTCACTCCCAAAGCTTGGATCCCTCTGTTGGCCTTGAGCCGCGAGGTCTTCTCCAATCCTACTTCTGCATCCCATTC
CATCTCTTTCCACGGTCTCCTTGGCGTCTCTTCGGAGTCAGTCCACAACATCCACCTCACTTATGGCGATGCCTTCCCAC
ATGGAGACTTCCGTGTTGTCTTTGGAGACTGCGGTATGACCAGTGAGGATGAACTTCATCACGAGGTTGCATCTCTCTCC
ACGAAGATGGAGTCTGCTCCTGATCGTTTGGTCTGGCTTGTGCCAAAGGATGTCCGCGAGAATGGTTGTCTTCACGCTTT
CTCGGAGGGCGTCCTCCTCGGTCGGTCTGAGCCTGTCGCTTTCACAGAGCCACTCCGGAAGCGCGAGTCTCTCTCTGAGA
TTGGTGACTCCGATGGCCTCTGGTTCAGCGGAATCCGCTATCTGCAGTCAAGCAACCTGACATCCGTCAAGGCCGCCGAA
GCTAAGGAAAAGAAGATTGGCATCGTTGGCGGTGGCATTTCCGGTCTGATGACGAGTCTGCTCCTGACTTCCGTCGGCAT
GACCAACTGGCACATCATTGAGGCGACTGAGCGTGTCGGAGGCCGCATCCGCACCAAGTATATGAATGGAACTAGTCCCG
ATGACTACCAGTACCAGGAGATGGGGCCCATGAGGTTCCCCGTTGAGGTCAAATACAACGACACCAACGAGACGCTGCCC
ATTCAGGATCACAAGATGGTCTTCCAGCTGGCTGAAGTCTTGAACGAGATGAACGGCAACGACACAGATCTCGCTGTCAA
GTTCATTCCCTGGACCCAGAACAATCCGAACACTCCCGCCAACTCTCGAGGATACCGCCTCCCTGATGCCGCATCCCTA
CCGCGGCCCAAATCGCCCAGAACCCCAGCATCTTCCGCGGCAGCTGCCAACGCGTCAGACCCCCAAGATGCGGAACTTGGC
AAGGAGTCCTTGGAGCGTCTCAGTGACCTTACCCCCGAGCGGATGCGCAACATCTCCGCCAACATCTTCAAGGCGCACCG
AGATGCCATTGACCGCGGCTTGTTTCACTGGTCTGAGGCAGCCTATCTCCGGTACCAGCTGGGCCTTGACGACGATACTG
TGGACTTCGTGGCTGCCTCCGACAACTATCCCATGTTCCCTGACTGGTGGCACGCGGTCTACTTCGCGGCCACGAAGTGG
CTCACGATCGACAAGGGCCTCGATTCGCTGTCAGGGCTTTTGTACCCCACGTCAAGGACAAGATCACGTACGGTCGCAA
GATTGAAGCCATGCAATGGAATGAGTCAACATCCAAGATCTCACTCGTCATGGAGGGAGAGCCCTCTTGCGGCGGCGAAGT
CCGATGAGTACGACTATGCTGTCGTCGCGGTGCCGTTCTCCAAGGTTCGTCTGTGGAAGCGGCCGGCTTACTCCAACCTC
TTGACGAGGGCTATTGGCAAGCTGAACTACGAGCAGGCCTGCAAA▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓GTTGCTCTGCTCTACGAGACACGCTTCTGGGAGCACCAGGAGATCCCCATCTTTGGAGGC
TGTGGCTCGGTTGATATCCCGGGTATTGGTGGCGTGTGCTACCCATCATACGAGATCAACTCCACGAGGCCTGGCGTGAT
TCTCTCTTCCTACATTACCGGCACAGAAGCCAGATCCGTGGTAGCCCTGAGCGAGGAAGATCACGTCGCCATGGTGCAGC
GTGCCATGGTCGAAGTCCACGGCCCTATGGCGGATGAGCAGTGGACCGGGATTTACGACCGTCTGTGCTGGGAGGTGGAT
GAGAACGCGGCCGGAGGCTGGGCTTCGCCGACAGTTGGCCAGCAGGAGCTGTTCATCCCGGCGTACCACAAGACGGAGCT
CAACACCATCTTCATCGGAGAGCACACGAGCATCACGCACGGGTGGATCTTCTCGGCCCTGGAATCGTCGGTCAGGGGCA
CGACGCAGTTGCTGCTCGATCTTGGTCTAGTGGATGAGGCGAAGCAGATTGTTGAGACTTGGATGGCGAGGTGGATCACC
GTTTGA
(NOTE: The gene for 'g10122' is located on the minus strand. The given sequence
is the reverse complement which translates the final protein product.)

SEQ ID NO: 4 g10122_Putative amino acid sequence
MFTPKAWIPLLALSREVFSNPTSASHSISFHGLLGVSSESVHNIHLTYGDAFPHGDFRVVFGDCGMTSEDELHHEVASLS
TRMESAPDRLVWLVPKDVRENGCLHAFSEGVLLGRSEPVAFTEPLRKRESLSEIGDSDGLWFSGIRYLQSSNLTSVKAAE
AREKKIGIVGGGISGLMTSLLLTSVGMTNWHIIEATERVGGRIRTKYMNGTSPDDYQYQEMGPMRFPVEVKYNDTNETLP
IQDHKMVFQLAEVLNEMNGNDTDLAVKFIPWTQNNPNTPANSRGYRLPDGRIPTAAQIAQNPSILPAAANASDPQDAELG
KESLERLSDLTPERMRNISANIFKAHRDAIDRGLFHWSEAAYLRYQLGLDDDTVDFVAASDNYPMFFDWWHAVYFAATKW
LTIDKGLDSLSRAFVPHVKDKITYGRKIEAMQWNESTSKISLSWRESPLAAAKSDEYDYAVVAVPFSKVRLWKRPAYSNL
LTRAIGKLNYEQACKVALLYETRFWEHQEIPIFGGCGSVDIPGIGGVCYPSYEINSTRPGVILSSYITGTEARSVVALSE
EDHVAMVQRAMVEVHGPMADEQWTGIYDRLCWEVDENAAGGWASPTVGQQELFIPAYHKTELNTIFIGEHTSITHGWIFS
ALESSVRGTTQLLLDLGLVDEAKQIVETWMARWITV

FIG. 6B

SEQ ID NO: 5
Codon-modified g4462 (penox1)
ATGAAGTCTCCATCTCTGGCTGTGGCTGGTCTCCTGCTTGGATCCTCTAGCCTCTCGCATGCCACCCAGCTGCGCATCGA
AACTCGTAAGTCGCTCAACTCCCGCATCGCTAATGTGCATATCGATGTTGACGCCCCTGTCGGCTCACCAGGTCGTGTTCA
CCTACGGTCCCTGCGATTCCGAGTCTCAGGAAAACGCCCATCACGTTATCGCTCAGTCGCAGAAGCTCGAGGCACGGAAG
CCTCATCGCCTGATCTGGACTATGCCTAAGGATCTTCACCCCGATGACTGTATCTCTGCCTGGGGAGAATCTGGTGACTT
GCTCGGCCGGTCCGTGCCACAGAAGGTTGCTCATAAGGAGATGCGCCGTCGGAAGCGCGATGACTCTGACTACAGCATCC
CAATGAACTCGTCCTCTGGAATCGATGTGTATGGCCCGTGGTTCGACGGTGTTGCCCTGCTTGAGAAGTCCGATAACCAC
AATGTTGACGTCGAAGCCGCTAAGGCCAAGGAGATCGCTATCGTCGGAGCCGGCATGGCTGGCCTTACCACTTATTTCAT
CTTGTCGGAAGCCGGTCTTTCCAACTTGACCATCCTCGAAGCTTCTGGACGCCTGGGCGGTCGTGTGCGCACTGAATACC
TTTCTGGAGGCCCCGTGATCACAGCTATGCCGAGATGGGCCCTATGCGTATCCCCTACCAGGCCCGGTTCGGTGATAAG
GCTTATAATATCAGCGACCAGGCTATCTTCTTCCGCCTCGTCGAGAAGGTTAACGAGCGCAATAAGAAGCTTGGAAACAC
CAAGGACCTGATCAATCTTATCCCTTTCATCCAGAGCTCGCCCAACGGACTGGCCTACTATCAGGGCAACAAGTTGGAAA
ATGGTCTCCCTCCCACTCAAGCTGATGTGGCTGCTGACCCAGCTCTCGGTAATGAGTCGCCAGAAATTCCTGAGTCTGCT
CAAGAATTGGCTGCTCAGCTTCAGCGTGCTTTGCCGAACGCTGAATTCCTTGAGTTGATGGCCACCAATTTCTGGCAGGC
CCATGCTGAATTCTTGGAGAACCAGGGTCCAGCTGGACTCCCGGCCGATCAGTGGTCTGAGTTCGCCTTCCTCGTCAACT
ACCTGAATGCTACCGTTTTCGACGCCAATGCTGTCACTGGTGGATATGATTGGCATTCCTCTCTTGACCGCAGCTCGTTG
GTTGGCATGAACTTGCTCCCAAATGCCTTCCACCCGTTGGTCGATGACATCACCAAGTTCAACGCTAAGGTCGAAAAGGT
GCAGCTCGATGAGAAGACCCTCTCGCCTCAAGCTGCACTGGCGTGCCAATTACACTGATCCAGAGTTGGAAAGCCAGTCGT
TCGACTATGCCATCCTCAGCCCTACCATGCCCGCTGTCCAGAAGCTTCGTTTGCCAGGCTTGCCGTTCGCCATGCGGAAC
GCTGTCGACTCTATGCCTTACGCCAGCGCTTGCAAGGTGGCTCTTGAATATCGTACTCGGTTCTGGGAGAAGTTCGATAA
TCCCATCTACGGTTCCTGCTCTACCAGCACTGACATCCCAGGTATCGGATCCGTTTGTTATCCGTCCTCTAACATCAATG
GCTCCGGTCCGGCCTCTCTGCTTGCTAGCTACGAAATTGGACGTCCTTATGGTGCTGAGTGGGCTGGCATCCCCGAGGAA
CAGCATGTTCAGTACGTCATCGATGCCATGATCGACATCCACGGAGAAGTCGCTCGCCGTGAGTTCACCGGCAAGTGCAA
GCGTAAGTGTTGGGCCCTGGATGAGTTCTCTAACGGCGGTTGGCCTCTCCAACCGTGGGAAATCATGAAACTTACCTTC
CGTCGTCTTCGAGACTCATTCCCACATGATCTTCGTTGGCGAACATACCTCGTATACTCACGCCTGGATCGCCTCGGCT
ATCGAGTCCGCTGTCCGTGGTTCCGTGCAGTTGCTCCTGGAACTCGGACTGATCGATGAGGCCAAGGACGTTGTCAACAC
CTGGATGGCTCGGTGGATCTCGGTGGTTCCGATCTGTCTAAGGCCGTCGTGAGCGGTGCCTCGGCTTGA SEQ ID NO: 6
Codon-modified g10122 (penox2)
ATGTTCACTCCTAAGGCTTGGATTCCACTCCTGGCTCTGAGCCGCGAGGTCTTCTCGAACCCTACCTCTGCCTCTCATAG
CATCTCGTTCCACGGACTTTTGGGCGTCTCCTCTGAATCTGTGCATAATATCCACCTTACCTACGGTGACGCTTTCCCCC
ATGGAGATTTCCGTGTCGTGTTCGGTGACTGCGGAATGACTTCTGAGGATGAACTGCATCACGAGGTCGCCTCCCTTTCT
ACCAAGATGGAAAGCGCTCCAGACCGCCTCGTGTGGCTGGTTCCGAAGGATGTGCGTGAGAACGGATGTTTGCACGCCTT
CTCTGAAGGCGTCTCCTGGGTCGGAGCGAGCCTGTCGCTTCACTGAACCCTTGCGCAAGCGTGAGAGCCTCTCGGAAA
TCGGAGACTCTGATGGCCTGTGGTTCAGCGGCATCCGCTATCTGCAGAGCTCGAATCTTACCTCTGTCAAGGCCGCTGAG
GCCAAGGAAAAGAAGATCGGTATCGTGGCGGTGGAATCTCCGGACTTATGACCTCTCTTTTGCTCACTAGCGTGGGTAT
GACCAACTGGCATATCATCGAGGCTACCGAACGCGTTGGCGGTCGGATCCGCACTAAGTACATGAATGGAACCAGCCCTG
ATGACTACCAGTATCAGGAGATGGGCCCTATGCGTTTCCCCGTCGAGGTGAAGTATAACGACACCAATGAAACTCTCCCC
ATCCAGGATCACAAGATGGTGTTCCAGTTGGCCGAGGTTCTCAACGAAATGAACGGCAATGACACTGATTTGGCTGTCAA
GTTCATCCCATGGACTCAGAACAATCCTAACAGCCCTGCCAATAGCCGCGGCTACCGTCTCCCAGGACGGTCGTATCCCGA
CCGCCGCTCAGATCGCTCAGAACCCATCTATTTTGCCTGCTGCTAATGCTTTCTGACCCACAGGATGCTGAGCTTGGC
AAGGGAGTCGCTTGAACGGTTGTCCGATCTCACTCCGGAACGTATGCGGAACATCTCGCCAATATCTTCAAGGCCCATCG
TGACGCTATCGATCGGGGTCTGTTCCACTGGTCCGAGGCTGCCTACCTTCGCTATCAGCTCGGACTGGATGACGATACCG
TCGACTTCGTGGCTGCCTCCGATAACTACCCAATGTTCCCGGACTGGTGGCATGCTGTGTATTTCGCTGCCACCAAGTGG
CTGACTATCGACAAGGCCTGGATTCCCTTTCTCGGGCCTTCGTTCCACACGTCAAGGATAAGATCACTTACGGTCGCAA
GATCGAGGCTATGCAGTGGAATGAAAGCACCTCGAAGATCTCCCTTTCCTGGCGTGAGTCGCCGCTCGCTGCTGCTAAGT
CCGACGAATACGATTATGCCGTTGTCGCTGTTCCATTCTCTAAGGTCCGTCTGTGGAAGCGTCCTGCCTATTCCAACCTG
CTTACTCGCGCTATCGGCAAGCTTAATTACGAGCAGGCCTGCAAGGTGGCTTTGCTCTATGAAACCCGTTTCTGGGAGCA
TCAGGAAATCCCAATCTTCGGAGGCTGCGGATCGGTGGATATCCCTGGCATCGGTGGAGTTTGTTACCCCTCTTATGAGA
TCAACAGCACCCGTCCGGGAGTTATCTTGTCCTCTTATATCACCGGCACTGAAGCCCGGTCGGTGGTTGCTCTCTCCGAG
GAAGACCATGTGGCCATGGTTCAGCGGGCTATGGTTGAGGTCCACGGTCCCATGGCCGATGAACAGTGGACTGGAATCTA
CGACCGCCTCTGTTGGGAAGTCGATGAAAATGCTGCTGGCGGTTGGGCTTCTCCTACTGTTGGACAGCAGGAGTTGTTCA
TCCCCGCTTATCACAAGACCGAGCTCAATACTATCTTCATCGGCGAACATACCTCGATCACTCACGGTTGGATCTTCTCC
GCCCTGGAGAGCTCGGTTCGTGGCACCACTCAGCTGCTTTTGGACCTTGGTTTGGTCGATGAGGCCAAGCAGATCGTGGA
AACTTGGATGGCTCGGTGGATCACCGTCTGA

FIG. 6C

SEQ ID NO: 7
Ptef
TGTGGACCAGACAGGCGCCACTCGGCCGGGCCACAACTGCTTGGGTTTTGACCGGGAGCGGACCAATTAAGGACTCGAAC
GACCGCGGGGTTCAAATGCAAACAAGTACAACACGCAGCAAACGAAGCAGCCCACCACTGCGTTGATGCCCAGTTTGTCT
GTCCGAAATCCACCGGAAAGGTGGAAACATACTATGTAACAATCAGAGGGAAGAAAAATTTTTATCGACGAGGCAGGAT
AGTGACTGATGGTGGGGTCATGGTCGGGTCTCCGAGCGAAAGAGAACCAAGGAAACAAGATCAACGAGGTTGGTGTACCC
AAAAGGCCGCAGCAACAAGAGTCATCGCCCAAAAGTCAACAGTCTGGAAGAGACTCCGCCGTGCAGATTCTGCGTCGGTC
CCGCACATGCGTGGTGGGGGCATTACCCCTCCATGTCCAATGATAAGGGCGGCGGTCGAGGGCTTAAGCCCGCCCACTAA
TTCGCCTTCTCGCTTGCCCCTCCATATAAGGATTCCCTCCTTCCCCTCCCACAACTTTTTTCCTCTTTCTCTCTTCGTC
CGCATCAGTACGTATATCTTTCCCCCCTACCTCTTTCTCACTCTTCCTCGATTCATTCCACTCTTCTCCTTACTGACATC
TGTTTTGCTCAGTACCTCTACGCGATCAGCCGTAGTATCTGAGCAAGCTTTTTTACAGAATCTTTCTAGTATCTTACAAA
GAACTACAAAGTTCGCACCACCTTCAAA SEQ ID NO: 8
Talp
GTACCAGGAGTACATTGGAGAGTTCTACCATTGTTGCTGGAATACAATGATGATTAGAAACCGAAGAGTGTTATGATTCG
GACGGATATACGCATGGCACGCATACAGCGTGATACATAGGCTGTTTGCTCAAGAATTAGGATTTTATCTGAATCCATGT
ACAGAGTTTACTTATGTTAGTAGTCAATGAAATCTTGGCTTTCTAATTTTGTCCGATCTACAAGGGGTAGTCGATCACAG
AACGAACTAGATGTGCAGGGAACGATGATCACCCGCTCTTAGCAAGACCTCTAGTAGTTTTCGACCATAGCTTTAACGCG
AATCATGACCCTACTATTTTCTAGATTGCAGACCAAGTCACATGACAATGTCCTCTTTGAAGTAGGATCAGTAGCTGATT
AGATTCCGGGAAATGAATTAGGGCTGGCGTTCCAACTACTGGGGAGTGCCGATGTTGCTGTATGAAAGATAGTAAGATTA
CTAGTGCACAGCTGTAGTAATTATTTACTCTAGATTATATATTCCAAATAATAAGTAATCTAAGATAGTAGACAGTCCTA
TGATATAGCTCCGGGTTCGAAGTCGGCAAAAGATATGCAATCACCTGTCGGGATGATATATGTATATCTGAAATACCGAC
ATCAACCATCCAGTCGGATCAGCTAAACGAAGTATCACTTCTTTCGCCACTGCCAATCACTACTTCTATTAAAGTTCATG
TTACAGTATAAGCCACAAGACTTATCTCCAGAACTAACTTGTGCATAGGAGCTCTGCCGATAGCCGGGTGGTTGGATCGG SEQ ID NO: 9
pyrG3
TAAGTACTCATTTATACAATAGTTGCAGAACCCCGCGCTACCCCTCCATTGCCAACATGTCTTCCAAGTCGCAATTGACC
TACAGCGCACGCGCTAGCAAGCACCCCAATGCGCTCGTGAAGAAGCTCTTCGAGGTTGCCGAGGCCAAGAAAACCAATGT
CACCGTTTCCGCCGACGTGACAACCACCAAAGAGCTGCTGGATTTGGCTGACCGTATGCGCACCGGGGATGCCACTTACA
TATGATCTAGTAATGGTTAATGGTGGAATATATAACAGGACTCGGTCCGTACATTGCCGTGATCAAAACTCACATCGATA
TCCTCTCCGATTTCAGCGAAGAGACCATCATCGGTCTGAAGGCCCTTGCAGAGAAGCACAATTTCCTCATCTTCGAAGAT
CGCAAGTTCATCGATATCGGAAACACAGTCCAAAGCAGTACCATGGCGGCACTCTGCGCATCTCTGAGTGGGCCCACAT
CATCAACTGCAGTATTCTGCCCGGTGAGGGTATCGTCGAGGCTCTGGCCCAGACTGCTTCGGCCGAGGACTTCCCCTATG
GCTCTGAGAGGGGCCTTTTGATCCTTGCGGAGATGACATCCAAGGGATCTTTGGCTACCGGTCAATATACTACTTCTTCT
GTTGACTATGCCCGGAAGTATAAGAAGTTTGTGATGGGATTCGTCTCGACGCGTCACCTGGGCGAGGTTCAGTCTGAAGT
TAGCTCGCCTTCGGAGGAGGAGGATTTCGTCGTCTTCACGACAGGTGTCAACCTCTCCTCGAAGGGAGACAAACTGGGAC
AGCAATACCAGACTCCTGAGTCTGCTGTTGGACGCGGTGCCGACTTTATCATTGCTGGTCGTGGAATTTATGCTGCTCCT
GATCCCGTGGAGGCAGCGAAGCGGTACCAGAAAGAGGGATGGATGCATACCAGAAGCGTGTTGGTGCGCAATAAGTAGT
GGTGAATACGTGCTCTTTTTATGGCAGTATATCGCAAGTATGATGCGATTCATAAATTCAGCAGTCGAATTCTACGAGAG
AACGATGCTAAGAGATACCCTCTCTATATGAATAATATGCCTGCCTCGAGATATGGACATATTCAAGATCAGAGTTAAGG
GTCATGTTTCAAAATCACACCAATCTCCAACATAGACGAGAATTTTTACCGGATTGTCTGAAGGTGCAGCTGGAGATTGG
TCTATTTTCTAAGAGTGGGGTATCACTAATGTACAGTCGGTCACTATCGTACAAACAATCACAATTATATACAAGATTTC
CCATCACCCCTTACTCTAACATGGCACTTTTATCCATCGAGTCCGAGCCTAGCCACCATTTGGTGCTTTCGTAGAGACCA
AAGTATAACCCTGATCCGACAGCGGCCATAAACGTGTTGATAGCACACCCTCGGAATAGTCCTCTCGGGCCATCTGTTCG
TATAATCTCCCGTACGGTATTGATCATCCTTTTCTTCTGAGGTGCGG SEQ ID NO: 10
Ptef-Rv
AGATGGAGACTTCATtttgaaggtggtgcgaactttgtag SEQ ID NO: 11
Talp-Fw
GGTGCCTCGGCTTGAgtaccaggagtacattggagagt

FIG. 6D

SEQ ID NO: 12
AHDRNPLEECFRETDYEEFLEIAKNGLTATSNPKRVVIVGAGMAGLSAAYVLAGAGHQVTVLEASERVGGRVRTYRKKDW
YANLGPMRLPTKHRIVREYIKKFDLKLNEFSQENENAWYFIKNIRKRVREVKNNPGLLEYPVKPSEEGKSAAQLYVESLR
KVVEELRSTNCKYILDKYDTYSTKEYLLKEGNLSPGAVDMIGDLLNEDSGYYVSFIESLKHDDIFGYEKRFDEIVGGMDQ
LPTSMYEAIKEKVQVHFNARVIEIQQNDREATVTYQTSANEMSSVTADYVIVCTTSRAARRIKFEPPLPPKKAHALRSVH
YRSGTKIFLTCTKKFWEDDGIRGGKSTTDLPSRFIYYPNRNFTSGVGVIIAYGIGDDANFFQALDFKDCADIVINDLSLI
HELPKEDIQTFCRPSMIQRWSLDKYAMGGITTFTPYQFQHFSEALTAPFKRIYFAGEYTAQFHGWIDSTIKSGLTAARDV
NRASENPSGIHLSNDNEF

SEQ ID NO: 13
AHDRNPLEECFRETDYEEFLEIAKNGLTATSNPKRVVIVGAGMAGLSAAYVLAGAGHQVTVLEASERVGGRVRTYRKKDW
YANLGPMRLPTKHRIVREYIKKFDLKLNEFSQENENAWYFIKNIRKRVREVKNNPGLLEYPVKPSEEGKSAAQLYVESLR
KVVKELKRTNCKYILDKYDTYSTKEYLLKEGNLSPGAVDMIGDLLNEDSGYYVSFIESLKHDDIFGYEKRFDEIVGGMDQ
LPTSMYEAIKEKVQVHFNARVIEIQQNDREATVTYQTSANEMSSVTADYVIVCTTSRAARRIKFEPPLPPKKAHALRSVH
YRSGTKIFLTCKKKFWEDDGIRGGKSTTDLPSRFIYYPNHNFTSGVGVIIAYGIGDDANFFQALDFKDCADIVINDLSLI
HQLPKEDIQTFCRPSMIQRWSLDKYAMGGITTFTPYQFQHFSEALTAPFKRIYFAGEYTAQFHGWIDSTIKSGLTAARDV
NRASENPSGIHLSNDNEF

SEQ ID NO: 14
MDNVDFAESVRTRWAKRLIREKVAKELNILTERLGEVPGIPPPREGRFLGGGYSHDNLPSDPLYSSIKPALLKEAPRAEE
ELPPRKVCIVGAGVSGLYIAMILDDLKIPNLTYDIFESSSRTGGRLYTHHFTDAKHDYYDIGAMRYPDIPSMKRTFNLFK
RTGMPLIKYYLDGENTPQLYNNHFFAKGVVDFYMVSVANGGTVPDDVVDSVGEKLQQAFGYYKERLAEDFDKGFDELMLV
DDMTTREYLKRGGPKGEAPKYDFFAIQWMETQNTGTNLFLQAFSEESVIDSFDFDNPTKPEWYCIEGGTSLLVDAMKETLV
HKVQNNKRVEAISIDLDAPDDGRMSVKIGGKDYSGYSTVFNTTALGCLDRMDLRGLNLHPTQADAIRCLHYDNSTKVALK
FSYPWWIKDCGITCGGAASTDLPLRTCVYPSYNLGDTGEAVLLASYTWSQDATRIGSLVKDAPPQPPKEDELVELILQNL
ARLHAEHMTYEGYIKEAYTGVYHAYCWANDPNVGGAFALFGPGQFSNLYPYLMRPAAGGKFHIVGEASSVHHAWIIGSLES
AYTAVYQFLYKYKMWDYLRLLLERWQYGLQELETGKHGTAHLQFILGSLPKEYQVKIV

FIG. 6E

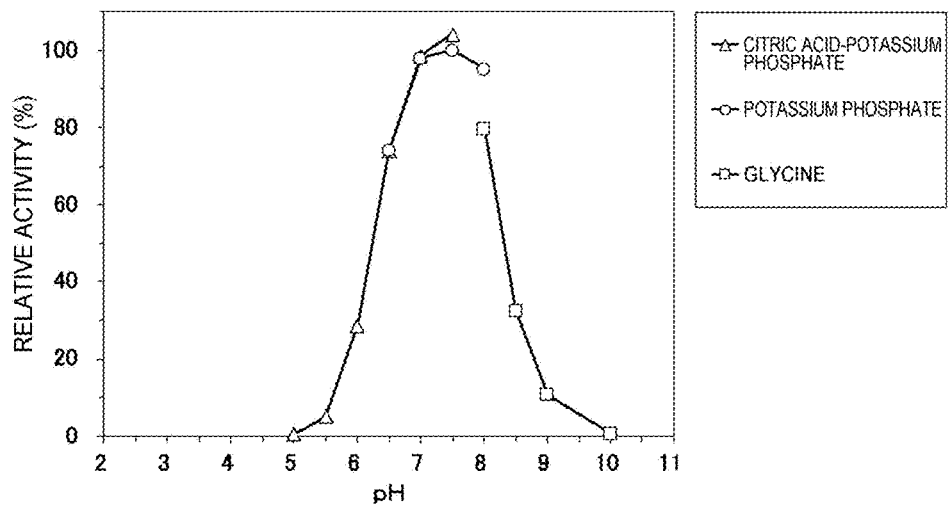

FIG. 7

ENZYME AND METHOD FOR ASSAYING PENTOSIDINE USING SAME

TECHNICAL FIELD

The present invention relates to pentosidine oxidase as a novel enzyme, and a method for measuring pentosidine using the pentosidine oxidase.

BACKGROUND ART

Pentosidine ((2S)-2-amino-6-[2-[[(4S)-4-amino-4-carboxybutyl]amino]imidazo[4,5-b]pyridin-4-yl]hexanoic acid) has a structure in which pentose, equimolar lysine and arginine are crosslinked, and is known to be accumulated in the skin of a human in correlation with aging or onset of diabetes. Particularly, pentosidine is known to increase at the time of the onset of diabetes or in a patient of end-stage nephropathy.

Pentosidine is known to be quantitatively determined by HPLC with its fluorescence (Ex: 335 nm, Em: 385 nm) used as an index after acid hydrolysis, and to be quantitatively determined by an immunochemical method (such as ELISA) using a monoclonal antibody against pentosidine.

Pentosidine is known to be relevant not only to aging and diabetes but also to schizophrenia. For example, a test method for schizophrenia including a step of measuring an amount of pentosidine in a biological sample has been disclosed (see, for example, Patent Literature 1).

CITATION LIST

Patent Literature

Patent Literature 1: Japanese Patent No. 5738346

SUMMARY OF INVENTION

Technical Problem

Quantitative determination of pentosidine by an immunochemical method or an instrumental analysis method may be complicated and expensive in some cases. An object of the present invention is to provide a novel enzyme, and a method for quantitatively determining pentosidine using the novel enzyme that is inexpensive and simple as compared with the immunochemical method or the instrumental analysis method.

Solution to Problem

The present inventors identified a novel enzyme from a filamentous fungus, and examined the activity thereof. As a result, it was found that the novel enzyme is useful for quantitative determination of pentosidine, and thus, the present invention was accomplished.

The outline of the present invention is as follows:

[1] A protein having activity of oxidatively degrading pentosidine.

[2] A protein having the following physicochemical properties:
  (1) activity: oxidatively degrading pentosidine; and
  (2) a molecular weight as measured by SDS-PAGE: 75,000 to 85,000.

[3] The protein according to [1] or [2], wherein the protein is selected from the group consisting of the following (a) to (f):
  (a) a protein consisting of an amino acid sequence as set forth in SEQ ID NO: 2 or 4;
  (b) a protein encoded by a gene consisting of a nucleotide sequence as set forth in SEQ ID NO: 1, 3, 5 or 6;
  (c) a protein consisting of an amino acid sequence having an identity of 75% or more with the amino acid sequence as set forth in SEQ ID NO: 2 or 4;
  (d) a protein encoded by a gene consisting of a nucleotide sequence having an identity of 75% or more with the nucleotide sequence as set forth in SEQ ID NO: 1, 3, 5 or 6;
  (e) a protein consisting of an amino acid sequence having deletion, substitution and/or addition of one or more amino acids of the amino acid sequence as set forth in SEQ ID NO: 2 or 4; and
  (f) a protein encoded by a nucleotide sequence that hybridizes under stringent conditions with the nucleotide sequence as set forth in SEQ ID NO: 1, 3, 5 or 6.

[4] The protein according to any of [1] to [3], wherein the activity is: activity of generating a deaminated product of pentosidine, hydrogen peroxide and ammonia; or activity of consuming oxygen.

[5] The protein according to any one of [1] to [4], derived from a filamentous fungus.

[6] The protein according to any of [1] to [5], having an optimum pH of about pH 6.5 to 8.0.

[7] The protein according to any of [1] to [6], having an optimum temperature of about 37 to 50° C.

[8] The protein according to any of [1] to [7], wherein 90% or more of the activity is retained after storage at 30° C. for 10 minutes.

[9] The protein according to any of [1] to [8], wherein 60% or more of the activity is retained in a pH range of pH 4.0 to 9.0.

[10] The protein according to any of [1] to [9], wherein a Km value for pentosidine is 1 mM or less.

[11] A gene encoding the protein according to any of [1] to [10].

[12] The gene according to [11], wherein the gene is selected from the group consisting of the following (a) to (f):
  (a) a gene consisting of a nucleotide sequence as set forth in SEQ ID NO: 1, 3, 5 or 6;
  (b) a gene encoding an amino acid sequence as set forth in SEQ ID NO: 2 or 4;
  (c) a gene consisting of a nucleotide sequence having an identity of 75% or more with the nucleotide sequence as set forth in SEQ ID NO: 1, 3, 5 or 6;
  (d) a gene encoding a protein consisting of an amino acid sequence having an identity of 75% or more with the amino acid sequence as set forth in SEQ ID NO: 2 or 4;
  (e) a gene encoding a protein consisting of an amino acid sequence having deletion, substitution and/or addition of one or more amino acids of the amino acid sequence as set forth in SEQ ID NO: 2 or 4; and
  (f) a gene consisting of a nucleotide sequence that hybridizes under stringent conditions with the nucleotide sequence as set forth in SEQ ID NO: 1, 3, 5 or 6.

[13] A kit comprising the protein according to any of [1] to [10], or the gene according to [11] or [12].

[14] A recombinant vector comprising the gene according to [11] or [12].

[15] A transformant comprising the vector according to [14].

[16] A method for producing the protein according to any of [1] to [10] by using the transformant according to [15].

[17] A method for measuring pentosidine, comprising:
contacting the protein according to any of [1] to [10] with a specimen; and
detecting a change caused by the contact.

[18] The method according to [17], wherein a change in an amount of oxygen, hydrogen peroxide or ammonia is detected in the detecting step.

[19] A method for producing a reaction product of pentosidine, comprising contacting the protein according to any of [1] to [10] with pentosidine.

[20] The method according to [19], wherein the reaction product is hydrogen peroxide or ammonia.

Advantageous Effects of Invention

Without intending to be bound by any theory, it is presumed that a novel enzyme, pentosidine oxidase, having been identified by the present inventors oxidatively degrades pentosidine to generate hydrogen peroxide and ammonia as shown in FIG. 5. Hydrogen peroxide can be easily detected or quantitatively determined through a peroxidase reaction or the like by a colorimetric method, a fluorescence method, a chemiluminescence method, an electrode method or the like, and hence, according to the present invention, pentosidine can be easily and rapidly detected and quantitatively determined by an enzymatic method.

BRIEF DESCRIPTION OF DRAWINGS

FIG. 6A illustrates sequences of SEQ ID NOS: 1 and 2.
FIG. 6B illustrates sequences of SEQ ID NOS: 3 and 4.
FIG. 6C illustrates sequences of SEQ ID NOS: 5 and 6.
FIG. 6D illustrates sequences of SEQ ID NOS: 7 to 11.
FIG. 6E illustrates sequences of SEQ ID NOS: 12 to 14.
FIG. 7 illustrates a range of optimum pH of PenOX2.

DESCRIPTION OF EMBODIMENT

Figure 1:
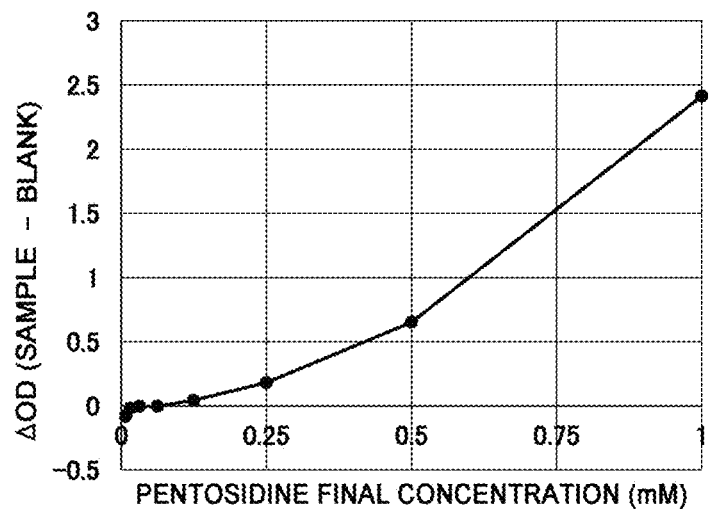
FIG. 1 illustrates a result of a substrate dose-dependence test of a crudely purified enzyme solution (Elution 1) fractionated by anion exchange chromatography from *Sarocladium* sp. ΔOD (ordinate) against a final pentosidine concentration (abscissa) is plotted. Data obtained 20 minutes after the start of a reaction is used.

Now, a protein and a gene encoding the same, a transformant, a production method and the like according to one aspect of the present invention will be described in detail. It is noted that the technical scope of the present invention is not limited to description made in this section but the present invention can be practiced in various forms as long as the objects thereof can be achieved.

The present invention provides a protein having pentosidine oxidase activity, a gene encoding the same, and the like. Pentosidine oxidase is a novel enzyme, and the enzyme activity thereof has not been completely elucidated yet, but the term "pentosidine oxidase activity" as used herein means activity of oxidatively degrading pentosidine, more specifically, activity of oxidizing pentosidine to generate a deaminated product thereof, hydrogen peroxide and ammonia, or activity of consuming oxygen. All proteins having such enzyme activity and genes encoding the same, without being limited by a specific sequence, are intended to be encompassed in the scope of the present invention. A nucleotide sequence and an amino acid sequence of pentosidine oxidase will now be, however, described by using, as an example, an enzyme derived from a filamentous fungus belonging to the genus *Sarocladium*.

(Amino Acid Sequence of Pentosidine Oxidase)

The gene of the present invention contains a nucleotide sequence encoding an amino acid sequence of pentosidine oxidase. The amino acid sequence of the pentosidine oxidase is not specifically limited as long as the pentosidine oxidase has the above-described enzyme activity. For example, one aspect of an enzyme having the pentosidine oxidase activity can be amino acid sequences as set forth in SEQ ID NOS: 2 and 4. Hereinafter, proteins having the amino acid sequences as set forth in SEQ ID NOS: 2 and 4 is also referred to as pentosidine oxidase 1 (or PenOX1) and pentosidine oxidase 2 (or PenOX2), respectively. It is predicted that a gene (g4462) encoding the pentosidine oxidase 1 consists of six exons and five introns, while a gene (g10122) encoding the pentosidine oxidase 2 consists of two exons and one intron. These enzymes are similar in having high substrate specificity to pentosidine and arginine, but are different in reactivity to the other L-amino acids.

The pentosidine oxidases having the amino acid sequences as set forth in SEQ ID NOS: 2 and 4 are derived from filamentous fungi belonging to the genus *Sarocladium*. Nucleotide sequences of genes encoding these enzymes are respectively set forth in SEQ ID NOS: 1 and 3. The amino acid sequences and the nucleotide sequences of the enzymes are shown in FIG. 6A to FIG. 6E.

The amino acid sequence of the pentosidine oxidase may contain, as long as it has the enzyme activity of the pentosidine oxidase explained above, an amino acid sequence having deletion, substitution, addition or the like, in the amino acid sequence of a wild type enzyme as set forth in SEQ ID NO: 2 or 4, of one to plural amino acids, for example, assuming that 100 amino acids in the amino acid sequence is regarded as one unit, 1, 2, 3, 4, 5, 6, 7, 8, 9, 10, 11, 12, 13, 14, 15, 16, 17, 18, 19, 20, 21, 22, 23, 24 or 25 amino acids, preferably a plurality of amino acids in each unit. Here, a range of the term "one to several" used in the expression "deletion, substitution or addition of one to several amino acids" is not specifically limited, and means preferably about 1, 2, 3, 4, 5, 6, 7, 8, 9 or 10, more preferably about 1, 2, 3, 4 or 5 in each unit. Besides, the term "deletion of an amino acid" means deletion or loss of an amino acid residue in the sequence, the term "substitution of an amino acid" means substitution of an amino acid residue with another amino acid residue in the sequence, and the term "addition of an amino acid" means addition of a new amino acid residue inserted into the sequence.

A specific form of the "deletion, substitution or addition of an amino acid" can be a form in which an amino acid is substituted with another chemically similar amino acid and yet the pentosidine oxidase activity is retained. Examples include a case where one hydrophobic amino acid is substituted with another hydrophobic amino acid, and a case where one polar amino acid is substituted with another polar amino acid having the same charge. Such chemically similar amino acids of each amino acid are known in this technical field.

Specifically, examples of a non-polar (hydrophobic) amino acid include alanine, valine, isoleucine, leucine, proline, tryptophan, phenylalanine and methionine. Examples of a polar (neutral) amino acid include glycine, serine, threonine, tyrosine, glutamine, asparagine and cysteine. Examples of a basic amino acid having a positive charge include arginine, histidine and lysine. Examples of an acidic amino acid having a negative charge include aspartic acid and glutamic acid.

Besides, the amino acid sequence of the pentosidine oxidase can be an amino acid sequence having a prescribed or higher sequence identity with the amino acid sequence of the wild type enzyme as set forth in SEQ ID NO: 2 or 4.

For example, it can be an amino acid sequence having a sequence identity, with the amino acid sequence of the pentosidine oxidase enzyme, of 75% or more, preferably 80% or more, more preferably 85% or more, still more preferably 90% or more, and most preferably 95% or more.

(Gene Encoding Pentosidine Oxidase)

The gene encoding the pentosidine oxidase (hereinafter sometimes referred to as the "pentosidine oxidase gene") is not specifically limited as long as it contains a nucleotide sequence encoding the amino acid sequence of the enzyme having the pentosidine oxidase activity. In some aspects, the pentosidine oxidase is produced by expression of the pentosidine oxidase gene in a transformant.

The term "expression of a gene" as used herein means that an enzyme encoded by the gene is produced, through transcription, translation or the like, in a form having original catalytic activity. Besides, the term "expression of a gene" embraces high level expression of the gene, namely, that the enzyme encoded by the gene is produced, by inserting the gene, in an amount exceeding original expression level of a host organism.

The pentosidine oxidase gene may be either a gene capable of, when introduced into a host organism, generating the pentosidine oxidase through splicing after transcription of the gene, or generating the pentosidine oxidase without splicing after transcription of the gene.

The pentosidine oxidase gene may not be completely identical to the gene that an origin organism such as a filamentous fungus belonging to the genus *Sarocladium* originally has (namely, a wild type gene), but may be a DNA having a nucleotide sequence that hybridizes under stringent conditions with a nucleotide sequence complementary to a nucleotide sequence of the wild type gene as long as it is a gene encoding the enzyme having the pentosidine oxidase activity.

The term "nucleotide sequence that hybridizes under stringent conditions" as used herein means a nucleotide sequence of a DNA obtained by using, as a probe, a DNA corresponding to a part of the nucleotide sequence of the wild type gene of SEQ ID NO: 1 or 3 by a colony hybridization method, a plaque hybridization method, a southern blot hybridization method or the like.

The term "stringent conditions" as used herein refers to conditions where a specific hybridization signal is clearly discriminated from a non-specific hybridization signal, and the conditions vary depending on a hybridization system employed, and the type, sequence and length of the probe used. Such conditions can be determined by changing the temperature of hybridization, or changing the temperature and a salt concentration employed in washing.

For example, when a non-specific hybridization signal is also strongly detected, the specificity can be increased by increasing the temperatures of hybridization and washing, and if necessary, decreasing the salt concentration employed in washing. Alternatively, when even a specific hybridization signal is not detected, the hybridization can be stabilized by decreasing the temperatures of hybridization and washing, and if necessary, increasing the salt concentration employed in washing.

In some aspects, a specific example of the stringent conditions is as follows. For example, a DNA probe is used as a probe, and hybridization is performed overnight (about 8 to 16 hours) by using 5×SSC, 1.0% (w/v) blocking reagent for nucleic acid hybridization (manufactured by Boehringer Mannheim), 0.1% (w/v)N-lauroyl sarcosine and 0.02% (w/v) SDS. Washing is performed twice for 15 minutes by using 0.1 to 0.5×SSC, 0.1% (w/v) SDS, preferably 0.1×SSC, 0.1% (w/v) SDS. The temperatures for performing the hybridization and the washing are 65° C. or higher, preferably 68° C. or higher.

Examples of a DNA having a nucleotide sequence that hybridizes under stringent conditions include a DNA that can be obtained by performing hybridization under the stringent conditions explained above using a filter on which a DNA having a nucleotide sequence of a wild type gene derived from a colony or a plaque, or a fragment of the DNA is immobilized; and a DNA that can be identified by washing the filter under a condition of 65° C. by using 0.1 to 1×SSC solution (1×SSC solution containing 150 mM sodium chloride and 15 mM sodium citrate) after performing hybridization at 40 to 75° C. in the presence of 0.5 to 2.0 M NaCl, preferably performing hybridization at 65° C. in the presence of 0.7 to 1.0 M NaCl. Preparation of a probe and method of hybridization can be performed in accordance with a method described in, for example, Moleular Cloning: A Laboratory Manual, 2nd-Ed., Cold Spring Harbor Laboratory, Cold Spring Harbor, N Y., 1989; and Current Protocols in Molecular Biology, Supplement 1-38, John Wiley & Sons, 1987-1997 (hereinafter, these literatures are also referred to as the "reference technical literatures").

Those skilled in the art can appropriately set conditions for obtaining a DNA having the nucleotide sequence that hybridizes under stringent conditions with the nucleotide sequence complementary to the nucleotide sequence of the wild type gene in consideration of various other conditions of a probe concentration, a probe length, a reaction time and the like in addition to the conditions of the salt concentration in the buffer, the temperature and the like.

An example of the DNA having the nucleotide sequence that hybridizes under stringent conditions includes a DNA having a prescribed or higher sequence identity with a nucleotide sequence of a DNA having a nucleotide sequence of a wild type gene used as a probe. It can be, for example, a DNA having a sequence identity, with the nucleotide sequence of the wild type gene, of 75% or more, preferably 80% or more, more preferably 85% or more, still more preferably 90% or more, and further preferably 95% or more.

The nucleotide sequence that hybridizes under stringent conditions with a nucleotide sequence complementary to the nucleotide sequence of the wild type gene embraces, for example, assuming that 500 bases in a nucleotide sequence is regarded as one unit, a nucleotide sequence having deletion, substitution, addition or the like, in the nucleotide sequence of the wild type gene, in each unit, of one to plural bases, for example, 1 to 125 bases, 1 to 100 bases, 1 to 75 bases, 1 to 50 bases, 1 to 30 bases, or 1 to 20 bases, preferably 1 to several bases, for example, 1, 2, 3, 4, 5, 6, 7, 8, 9 or 10 bases.

Here, the term "deletion of a base" means deletion or loss of a base in the sequence, the term "substitution of a base" means substitution of a base with another base in the sequence, and the term "addition of a base" means addition of a new base inserted into the sequence.

It is probable that an enzyme encoded by the nucleotide sequence that hybridizes under stringent conditions with a nucleotide sequence complementary to the nucleotide sequence of the wild type gene is an enzyme having an amino acid sequence having deletion, substitution, addition or the like of one to plural amino acids, preferably several amino acids in an amino acid sequence of an enzyme encoded by the nucleotide sequence of the wild type gene, and still has the same enzyme activity as the enzyme encoded by the nucleotide sequence of the wild type gene.

Besides, by utilizing the fact that there are several codons corresponding to one amino acid, a gene encoding the enzyme may be a nucleotide sequence encoding an amino acid sequence the same as or similar to an amino acid sequence of an enzyme encoded by the wild type gene, and may contain a nucleotide sequence different from the wild type gene. Examples of such nucleotide sequence obtained by codon modification of the nucleotide sequence of the wild type gene include a nucleotide sequence as set forth in SEQ ID NO: 5 (penox1) obtained by codon modification of g4462, and a nucleotide sequence as set forth in SEQ ID NO: 6 (penox2) obtained by codon modification of g10122 (FIG. 6C). A nucleotide sequence obtained by codon modification is preferably a nucleotide sequence in which codon modification is performed, for example, so as to be readily expressed in a host organism.

(Means for Calculating Sequence Identity)

A method for obtaining a sequence identity between nucleotide sequences or amino acid sequences is not specifically limited. The sequence identity can be obtained, for example, by aligning a wild type gene or an amino acid sequence of an enzyme encoded by the wild type gene with a target nucleotide sequence or amino acid sequence utilizing a commonly known method, and by using a program for calculating a concordance rate between these sequences.

As the program for calculating a concordance rate between two amino acid sequences or nucleotide sequences, for example, Karlin and Altschul algorithm (Proc. Natl. Acad. Sci. USA 87: 2264-2268, 1990; Proc. Natl. Acad. Sci. USA 90: 5873-5877, 1993) is known, and a BLAST program employing this algorithm has been developed by Altschul et al. (J. Mol. Biol. 215: 403-410, 1990). Furthermore, a program for determining a sequence identity with higher sensitivity than BLAST, Gapped BLAST, is also known (Nucleic Acids Res. 25: 3389-3402, 1997). Accordingly, those skilled in the art can search, in database, a sequence having a high sequence identity with a given sequence by utilizing, for example, the above-described program. These programs are available on, for example, the Internet website of National Center for Biotechnology Information, US (http://blast.ncbi.nlm.nih.gov/Blast.cgi).

While the above-described methods can be usually employed for searching a sequence having a sequence identity in database, as means for determining a sequence identity between individual sequences, homology search of Genetyx version 12.0.1, network version (manufactured by Genetyx Corporation) can be employed. This method is based on the Lipman-Pearson method (Science 227: 1435-1441, 1985). In analyzing a sequence identity between nucleotide sequences, a region encoding a protein (CDS or ORF) is used if possible.

(Origin of Gene Encoding Enzyme)

The gene encoding the enzyme is derived from species having pentosidine oxidase productivity. Examples of an origin organism of the gene encoding the enzyme include microorganisms such as filamentous fungi. Specific examples of the microorganisms having pentosidine oxidase productivity include those belonging to the genus *Sarocladium*.

As described above, the origin organism of the gene encoding the enzyme is not specifically limited, and it is preferable that the enzyme expressed in a transformant exhibits the activity without being inactivated depending on growth conditions of a host organism. Therefore, the origin organism of the gene encoding the enzyme is preferably a microorganism grown under similar growth conditions to a host organism to be transformed by inserting the gene encoding the enzyme.

Characteristic physicochemical properties of the enzyme having the pentosidine oxidase activity are exemplified as follows:

Molecular Weight as measured by SDS-PAGE: 75,000 to 85,000

Optimum pH: about pH 6.5 to 8.0 The optimum pH refers to pH at which the enzyme works optimally; the pentosidine oxidase can function at pH out of the above-described range.

Optimum Temperature: about 37 to 50° C.

The optimum temperature refers to a temperature at which the enzyme works optimally; the pentosidine oxidase can function at a temperature out of the above-described range.

Temperature Stability: When it is stored at 30° C. for 10 minutes, 90% or more of the pentosidine oxidase activity is retained. When it is stored at 40° C. for 10 minutes, 50% or more of the pentosidine oxidase activity is retained.

pH Stability: In a range of pH 4.0 to 9.0, 60% or more of the pentosidine oxidase activity is retained.

Km value: A Km value for pentosidine is 1 mM or less.

A Km value refers to a Michaelis constant. A method for calculating the Km value is not specifically limited, and any of known methods can be freely selected for the calculation. For example, a Km value can be calculated in accordance with the Michaelis-Menten equation drawn by the Lineweaver-Burk plot method as in a method described in Example 9 below.

(Cloning of Gene Encoding Enzyme by Genetic Engineering Method)

The gene encoding the enzyme can be inserted into any appropriate known vectors. Furthermore, the resultant vector may be introduced into an appropriate known host organism, and thus, a transformant into which a recombinant vector (recombinant DNA) containing the gene encoding the enzyme has been introduced can be produced. A method for obtaining the gene encoding the enzyme, a nucleotide sequence of the gene encoding the enzyme, a method for obtaining amino acid sequence information of the enzyme, a method for producing various vectors, a method for producing a transformant and the like can be appropriately selected by those skilled in the art. Besides, the terms "transformation" and "transformant" as used herein respectively embrace transduction and a transductant. An example of cloning of the gene encoding the enzyme will be unlimitedly described below.

For cloning the gene encoding the enzyme, a usual gene cloning method can be appropriately employed. For example, a chromosome DNA or an mRNA can be extracted from microorganisms or various cells having productivity of the enzyme by an ordinary method, for example, any of methods described in the reference technical literatures (described above). The mRNA thus obtained can be used as a template for synthesizing a cDNA. The chromosome DNA or cDNA thus obtained can be used for producing a library of the chromosome DNA or cDNA.

In some aspects, the gene encoding the enzyme can be obtained by cloning using, as a template, a chromosome DNA or cDNA of an origin organism having the gene. The origin organism of the gene encoding the enzyme is not specifically limited, and an example includes *Sarocladium* sp. described above. For example, *Sarocladium* sp. is cultured, a moisture content is removed from the microbial cell thus obtained, the resultant is physically ground using a mortar or the like under cooling in liquid nitrogen to obtain a microbial cell fragment in the form of a fine powder, and a chromosome DNA fraction is extracted from the microbial cell fragment by a usual method. In an operation for extracting a chromosome DNA, a commercially available chromosome DNA extraction kit such as DNeasy Plant Mini Kit (manufactured by Qiagen K.K.) can be used.

Subsequently, the chromosome DNA is used as a template for a polymerase chain reaction (hereinafter referred to as "PCR") using a primer complementary to a 5' terminal sequence and a 3' terminal sequence for amplifying the DNA. The primer is not specifically limited as long as a DNA fragment containing the gene can be amplified. Alternatively, a DNA containing a target gene fragment is amplified by appropriate PCR such as the 5' RACE method or the 3' RACE method, and the resultant DNAs are ligated to obtain a full-length DNA containing the target gene.

Besides, the method for obtaining the gene encoding the enzyme is not specifically limited, and instead of the genetic engineering method, a chemical synthesis method can be employed for constructing the gene encoding the enzyme.

A nucleotide sequence of an amplification product having been amplified by PCR or a chemically synthesized gene can be confirmed, for example, as follows: First, a DNA to be confirmed for the sequence is inserted into an appropriate vector by a usual method to produce a recombinant DNA. For cloning into a vector, a commercially available kit such as TA Cloning Kit (manufactured by Invitrogen); a commercially available plasmid vector DNA such as pUC19 (manufactured by Takara Bio Inc.), pUC18 (manufactured by Takara Bio Inc.), pBR322 (manufactured by Takara Bio Inc.), pBluescript SK+ (manufactured by Stratagene) or pYES2/CT (manufactured by Invitrogen); and a commercially available bacteriophage vector DNA such as λEMBL3 (manufactured by Stratagene) can be used. In some aspects, the recombinant DNA is used to transform a host organism, for example, *E. coli* (*Escherichia coli*), preferably *E. coli* JM109 (manufactured by Takara Bio Inc.) or *E. coli* DH5a (manufactured by Takara Bio Inc.). The recombinant DNA contained in the resultant transformant may be purified by using QIAGEN Plasmid Mini Kit (manufactured by QIAGEN K.K.) or the like.

A nucleotide sequence of each gene inserted into the recombinant DNA can be determined by a dideoxy method (Methods in Enzymology, 101, 20-78, 1983) or the like. A sequencer to be used in determining the nucleotide sequence is not specifically limited, and examples include Li-COR MODEL 4200L Sequencer (manufactured by Aloka Co., Ltd.), 370 DNA Sequence System (manufactured by PerkinElmer, Inc.) and CEQ2000XL DNA Analysis System (manufactured by Beckman). On the basis of the nucleotide sequence thus determined, an amino acid sequence of the protein to be translated, namely, the enzyme, can be known.

(Construction of Recombinant Vector Containing Gene Encoding Enzyme)

A recombinant vector (recombinant DNA) containing the gene encoding the enzyme can be constructed by ligating a PCR amplification product containing any one of genes encoding the enzyme with various vectors in such a manner that the gene encoding the enzyme can be expressed. For example, the recombinant vector can be constructed by using an appropriate restriction enzyme to cut out a DNA fragment containing any one of genes encoding the enzyme, and ligating the DNA fragment with a plasmid cut with an appropriate restriction enzyme. Alternatively, the recombinant vector can be obtained by ligating, using a commercially available kit such as In-Fusion HD Cloning Kit (manufactured by Clontech Laboratories, Inc.) for producing a recombinant vector, a DNA fragment containing the gene and having a sequence complementary to a plasmid added to both ends thereof with a DNA fragment derived from the plasmid amplified by inverse PCR.

(Method for Producing Transformant)

A method for producing a transformant is not specifically limited, and an example includes a method in which the gene encoding the enzyme is inserted by an ordinary method into a host organism in such a manner that the gene is expressed. In some aspects, a DNA construct in which any one of genes encoding the enzyme has been inserted between an expression-inducing promoter and a terminator is produced. Subsequently, a host organism is transformed by the DNA construct containing the gene encoding the enzyme, and thereby a transformant that overexpresses the gene encoding the enzyme can be obtained. Herein, a DNA fragment prepared for transforming a host organism, containing an expression-inducing promoter/a gene encoding the enzyme/a terminator, and a recombinant vector containing the DNA fragment are generically designated as a DNA construct.

A method for inserting the gene encoding the enzyme into a host organism in such a manner that the gene is expressed is not specifically limited, and examples include a method in which it is directly inserted into a chromosome of a host organism by utilizing homologous recombination or non-homologous recombination; and a method in which it is introduced into a host organism by ligating with a plasmid vector.

In the method utilizing homologous recombination, the DNA construct can be ligated between sequences homologous to an upstream region and a downstream region of a recombination site on a chromosome to be inserted into a genome of a host organism. In the method utilizing non-homologous recombination, even when the homologous sequence is not ligated with the DNA construct, the gene can be inserted into a genome of a host organism. A high expression promoter is not specifically limited, and examples include a promoter region of a translational elongation factor of TEF1 gene (tef1), a promoter region of α-amylase gene (amy), a promoter region of alkali protease gene (alp) and a promoter region of glyceraldehyde-3-phosphate dehydrogenase (gpd).

In the method utilizing a vector, a DNA construct is integrated, by an ordinary method, into a plasmid vector to be used for the transformation of a host organism, and thus, a corresponding host organism can be transformed by an ordinary method.

Such a suitable vector-host system is not specifically limited as long as it is a system where the enzyme can be produced in a host organism, and examples include a system of pUC19 and a filamentous fungus, and a system of pSTA14 (Mol. Gen. Genet. 218, 99-104, 1989) and a filamentous fungus.

Upon using the DNA construct, the DNA construct is preferably introduced into a chromosome of a host organism. Alternatively, it can be used without introduction into a chromosome when the DNA construct is integrated into an autonomous replication vector (Ozeki et al., Biosci. Biotechnol. Biochem. 59, 1133 (1995)).

The DNA construct may contain a marker gene with which a transformed cell can be selected. The marker gene is not specifically limited, and examples include a gene complementing an auxotrophy of a host organism such as pyrG, niaD or adeA; and a drug resistance gene resistant to a drug such as pyrithiamine, hygromycin B or oligomycin. Besides, the DNA construct preferably contains a promoter, a terminator or another control sequence (such as an enhancer or a polyadenylation sequence) with which the gene encoding the enzyme can be overexpressed in a host organism. The promoter is not specifically limited and can be an appropriate expression-inducing promoter or constitutive promoter, and examples include a tef1 promoter, an alp promoter, an amy promoter and a gpd promoter. The terminator is also not specifically limited, and examples include an alp terminator, an amy terminator and a tef1 terminator.

In the DNA construct, an expression control sequence for the gene encoding the enzyme is not always necessary when a DNA fragment containing the gene encoding the enzyme to be inserted has an expression control function. Besides, when the transformation is performed by a co-transformation method, the DNA construct may not contain a marker gene in some cases.

The DNA construct may be tagged for purification. For example, when a linker sequence is appropriately connected upstream or downstream of the gene encoding the enzyme to connect a nucleotide sequence of 6 codons or more encoding histidine, purification using a nickel column can be performed.

The DNA construct may contain a homologous sequence necessary for marker recycling. For example, with respect to a pyrG marker, when a sequence homologous to an upstream sequence of an insertion site (5' homologous recombination region) is added downstream of the pyrG marker, or when a sequence homologous to a downstream sequence of an insertion site (3' homologous recombination region) is added upstream of the pyrG marker, the pyrG marker can be lost on a medium containing 5-fluoroorotic acid (5FOA). The length of the homologous sequence suitable for the marker recycling is preferably 0.5 kb or more.

One aspect of the DNA construct is a DNA construct in which a tef1 gene promoter, the gene encoding the enzyme, an alp gene terminator and a pyrG marker gene are ligated with In-Fusion Cloning Site present in a multicloning site of pUC19.

One aspect of the DNA construct used when the gene is inserted through the homologous recombination is a DNA construct in which a 5' homologous recombination sequence, a tef1 gene promoter, the gene encoding the enzyme, an alp gene terminator, a pyrG marker gene and a 3' homologous recombination sequence are ligated.

One aspect of the DNA construct used when the gene is inserted through the homologous recombination and a marker is to be recycled is a DNA construct in which a 5' homologous recombination sequence, a tef1 gene promoter, the gene encoding the enzyme, an alp gene terminator, a homologous sequence for the marker recycling, a pyrG marker gene and a 3' homologous recombination sequence are ligated.

When the host organism is a filamentous fungus, a transformation method for the filamentous fungus can be appropriately selected from methods known to those skilled in the art. For example, a protoplast PEG method (see, for example, Mol. Gen. Genet. 218, 99-104, 1989 (mentioned above) and Japanese Patent Laid-Open No. 2007-222055) in which polyethylene glycol and calcium chloride are used after preparing a protoplast of the host organism can be employed. As a medium to be used for regenerating a transformant, an appropriate medium is used in accordance with a host organism and a transformation marker gene to be used. For example, when *Aspergillus oryzae* (*A. oryzae*) and *Aspergillus sojae* (*A. sojae*) are used as a host organism and the pyrG gene is used as the transformation marker gene, a transformant can be regenerated in, for example, a Czapek-Dox minimal medium (manufactured by Difco Laboratories Inc.) containing 0.5% agar and 1.2 M sorbitol.

Besides, for example, in order to obtain a transformant, the homologous recombination may be utilized to replace, with a high expression promoter such as tef1, a promoter of the gene encoding the enzyme that a host organism originally has on the chromosome. Also in this case, a transformation marker gene such as pyrG is preferably inserted in addition to the high expression promoter. For this purpose, for example, referring to an example described in Japanese Patent Laid-Open No. 2011-239681, a transformation cassette containing the whole or a part of an upstream region of the gene encoding the enzyme/a transformation marker gene/a high expression promoter/the gene encoding the enzyme can be used. In this case, the whole or a part of the upstream region of the gene encoding the enzyme and the gene encoding the enzyme is used for the homologous recombination.

As the whole or a part of the gene encoding the enzyme, those containing a region from a start codon to a middle region can be used. A length of the region suitably used for the homologous recombination is preferably 0.5 kb or more.

For confirming that a transformant has been prepared, the transformant is cultured under conditions where the enzyme activity of the enzyme is obtained, and then it is confirmed whether or not the target product is detected in a culture obtained after the culture.

Alternatively, whether or not a transformant has been prepared may be confirmed by extracting a chromosome DNA from the transformant, using the chromosome DNA as a template for performing PCR, and confirming an amplification of a PCR product that amplifies if the desired transformant has been prepared. In this case, the PCR is performed using, for example, a combination of a forward primer corresponding to a nucleotide sequence of a promoter used and a reverse primer corresponding to a nucleotide sequence of a transformation marker gene, and it is confirmed whether a product having an assumed length is produced.

When the transformation is performed through the homologous recombination, it is preferred that PCR is performed by using a combination of a forward primer positioned upstream from an upstream homologous region used and a reverse primer positioned downstream from a downstream homologous region used to confirm whether or not a product having a length assumed to be obtained when the homologous recombination is caused is produced.

(Host Organism)

The host organism is not specifically limited as long as it is an organism capable of producing the enzyme through the transformation using a DNA construct containing the gene encoding the enzyme. It can be a microorganism, a plant or the like, and examples of the microorganism include a microorganism belonging to the genus *Aspergillus*, a microorganism belonging to the genus *Escherichia*, a microorganism belonging to the genus *Saccharomyces*, a microorganism belonging to the genus *Pichia*, a microorganism belonging to the genus *Schizosaccharomyces*, a microorganism belonging to the genus *Zygosaccharomyces*, a microorganism belonging to the genus *Trichoderma*, a microorganism belonging to the genus *Penicillium*, a microorganism belonging to the genus *Rhizopus*, a microorganism belonging to the genus *Neurospora*, a microorganism belonging to the genus *Mucor*, a microorganism belonging to the genus *Acremonium*, a microorganism belonging to the genus *Fusarium*, a microorganism belonging to the genus *Neosartorya*, a microorganism belonging to the genus *Byssochlamys*, a microorganism belonging to the genus *Talaromyces*, a microorganism belonging to the genus *Ajellomyces*, a microorganism belonging to the genus *Paracoccidioides*, a microorganism belonging to the genus *Uncinocarpus*, a microorganism belonging to the genus *Coccidioides*, a microorganism belonging to the genus *Arthroderma*, a microorganism belonging to the genus *Trichophyton*, a microorganism belonging to the genus *Exophiala*, a microorganism belonging to the genus *Capronia*, a microorganism belonging to the genus *Cladophialophora*, a microorganism belonging to the genus *Macrophomina*, a microorganism belonging to the genus *Leptosphaeria*, a microorganism belonging to the genus *Bipolaris*, a microorganism belonging to the genus *Dothistroma*, a microorganism belonging to the genus *Pyrenophora*, a microorganism belonging to the genus *Neofusicoccum*, a microorganism belonging to the genus *Setosphaeria*, a microorganism belonging to the genus *Baudoinia*, a microorganism belonging to the genus *Gaeumannomyces*, a microorganism belonging to the genus *Marssonina*, a microorganism belonging to the genus *Sphaerulina*, a microorganism belonging to the genus *Sclerotinia*, a microorganism belonging to the genus *Magnaporthe*, a microorganism belonging to the genus *Verticillium*, a microorganism belonging to the genus *Pseudocercospora*, a microorganism belonging to the genus *Colletotrichum*, a microorganism belonging to the genus *Ophiostoma*, a microorganism belonging to the genus *Metarhizium*, a microorganism belonging to the genus *Sporothrix*, a microorganism belonging to the genus *Sordaria*, and a microorganism belonging to the genus *Arabidopsis*, and a microorganism and a plant are preferred. It is noted that a human is excluded from the host organism in any case.

Among the filamentous fungi, in consideration of safety and culture easiness, microorganisms belonging to the genus *Aspergillus* such as *Aspergillus oryzae*, *Aspergillus sojae*, *Aspergillus niger* (*A. niger*), *Aspergillus tamarii* (*A. tamarii*), *Aspergillus awamori* (*A. awamori*), *Aspergillus usami* (*A. usami*), *Aspergillus kawachii* (*A. kawachii*) and *Aspergillus saitoi* (*A. saitoi*) are preferred.

The expression of the protein of the present invention is not limited to the expression using the aforementioned host organism. For example, an in vitro cell-free protein expression system can be suitably used particularly when the expression is not for mass production of a commercial scale or the like. The cell-free protein expression system is also advantageous in that cell culture is not required and that the protein can be easily purified. In the cell-free protein expression system, a gene corresponding to the desired protein and a reaction solution containing a molecular mechanism of transcription and translation such as a cell lysate are principally used.

(Specific Examples of Gene Encoding Enzyme)

Examples of a gene encoding the enzyme derived from the genus *Sarocladium* include the genes g4462 and g10122 having the nucleotide sequences as set forth in SEQ ID NOS: 1 and 3, respectively. It is noted that the amino acid sequences of the pentosidine oxidase 1 protein (PenOX1) and the pentosidine oxidase 2 protein (PenOX2) are set forth in SEQ ID NOS: 2 and 4, respectively.

A method for obtaining a gene encoding the enzyme from an organism belonging to the genus *Sarocladium* or other organisms is not specifically limited. For example, the gene can be obtained by performing BLAST homology search for a genomic DNA of a target organism based on the nucleotide sequences (SEQ ID NOS: 1 and 3) of the genes g4462 and g10122 to specify a gene having a nucleotide sequence having a high sequence identity with the nucleotide sequences of the genes g4462 and g10122. Alternatively, the gene can be obtained by specifying, based on a total protein of a target organism, a protein having an amino acid sequence having a high sequence identity with the amino acid sequences (SEQ ID NOS: 2 and 4) of the pentosidine oxidase 1 and pentosidine oxidase 2 proteins, and specifying a gene encoding the specified protein.

The gene encoding the enzyme obtained from the genus *Sarocladium*, or the gene encoding the enzyme having the sequence identity with the enzyme can be introduced into an arbitrary host cell of a host organism such as a microorganism belonging to the genus *Aspergillus* for the transformation.

(Transformant)

One aspect of the transformant is a transformant obtained by inserting any one of the genes or a combination of the genes into a host organism such as a microorganism or a plant, and transforming the resultant for expressing the inserted gene.

Another aspect of the transformant is a transformant obtained by inserting, into a host organism such as a microorganism or a plant, a gene (containing a promoter sequence and the like excluding ORF) containing the whole or a part of the gene g4462 or g10122, and a DNA construct designed to express, at a high level or a low level, a transcription factor controlling transcription of the gene, and transforming the resultant for expressing the inserted gene.

When the host organism is an organism having pentosidine oxidase productivity such as the genus *Sarocladium*, it is preferable that the inserted gene is constantly forcedly expressed or expressed at a higher level than in endogenous expression, or conditionally expressed at a later stage of the culture after cell proliferation. Owing to the function of the transcription factor changed in its expression level, when cultured or grown under conditions suitable to the host organism or the transformant, such a transformant can produce pentosidine oxidase in a detectable or larger amount even when the host organism does not produce pentosidine oxidase or produces a slight amount of pentosidine oxidase.

(Production Method)

A production method according to another aspect of the present invention is, for example, a method in which pentosidine oxidase is produced by culturing a transformant using a medium suitable for the growth of the transformant under culture conditions suitable for the growth of the transformant. A culture method is not specifically limited, and when the host organism is a filamentous fungus, examples include a solid culture method and a liquid culture method performed under or without air stream.

The production method according to still another aspect of the present invention is a method for producing pentosidine oxidase extracted from a transformant. In the following, a production method employed when a host organism and a wild type organism are filamentous fungi will be principally described, nevertheless, it is noted that the production methods according to the various aspects of the present invention are not limited by the following description.

As a medium, either one of a synthetic medium and a natural medium can be used as long as it is a medium usually used for culturing a host organism and a wild type organism (hereinafter sometimes generically referred to as the "host organism and the like"), namely, one containing a carbon source, a nitrogen source, an inorganic substance and other nutrients at a proper ratio. When the host organism and the like are microorganisms belonging to the genus *Aspergillus*, a YMG medium, a PPY medium and the like as described in examples below can be used, but the medium is not specifically limited.

As the culture conditions for the transformant, culture conditions for the host organism and the like usually known to those skilled in the art may be employed. For example, when the host organism and the like are filamentous fungi, the culture conditions can be appropriately set, for example, with initial pH of the medium adjusted to 5 to 10, a culture temperature set to 20 to 40° C., and a culture time set to several hours to several days, preferably 1 to 7 days, more preferably 2 to 4 days and the like. Culturing means is not specifically limited, and aerated and agitated submerged culture, shaking culture, static culture or the like can be employed, and the culture is performed preferably under conditions where dissolved air is adequately present. For example, one example of the medium and the culture conditions to be employed for culturing a microorganism belonging to the genus *Aspergillus* includes shaking culture using a YMG medium or PPY medium performed at 30° C. and 160 rpm for 3 to 5 days as described in examples below.

A method for extracting pentosidine oxidase from a culture after completing the culture is not specifically limited. For the extraction, a microbial cell collected from the culture by filtration, centrifugation or the like may be directly used, or the microbial cell thus collected may be dried or further ground before use. A drying method for the microbial cell is not specifically limited, and examples include freeze drying, sun drying, hot air drying, vacuum drying, through flow drying and reduced pressure drying.

Alternatively, instead of the aforementioned treatment, the microbial cell may be subjected to a microbial cell disruption treatment such as a method for destroying the microbial cell using destruction means such as an ultrasonic disintegrator, a French press, a Dyno-mill or a mortar; a method for degrading a cell wall of the microbial cell using a cell wall degrading enzyme such as yatalase; or a method for degrading the microbial cell by using a surfactant such as SDS or Triton X-100. Any of these methods can be employed alone or in combination.

The extract thus obtained is subjected to a purification treatment such as centrifugation, filtration, ultrafiltration, gel filtration, separation using a solubility difference, solvent extraction, chromatography (adsorption chromatography, hydrophobic chromatography, cation exchange chromatography, anion exchange chromatography, reverse phase chromatography or the like), crystallization, an activated carbon treatment, a membrane treatment or the like, and thus, a target product can be purified.

In the production method of each aspect of the present invention, various arbitrary procedures or operations can be additionally performed before, after or during any of the aforementioned steps as long as the problems of the present invention can be solved.

(Measurement Method)

A method for measuring pentosidine of the present invention includes the steps of: contacting pentosidine oxidase with a specimen; and detecting a change caused by the contact.

The term "specimen" as used herein means a sample of blood, body fluid, excretion or the like derived from a subject, such as a target affected by or suspected to be affected by a disease related to pentosidine. The specimen may not always contain pentosidine, and even when pentosidine is not contained, the measurement method of the present invention can be employed for analysis (qualitative analysis) for the presence or absence of a pentosidine. The term "change caused by the contact" as used herein means a change over time of the presence or absence, or the amount of a starting material such as pentosidine contained in the specimen, or a reaction product or a substance consumed in a reaction with pentosidine oxidase.

In a more specific aspect, a method for measuring pentosidine can include the steps of: (A) reacting pentosidine oxidase with a specimen in the presence of water and oxygen; and (B) measuring an amount of at least one of a reaction product and a substance consumed in a reaction resulting from the reaction of the pentosidine oxidase.

Figure 5:
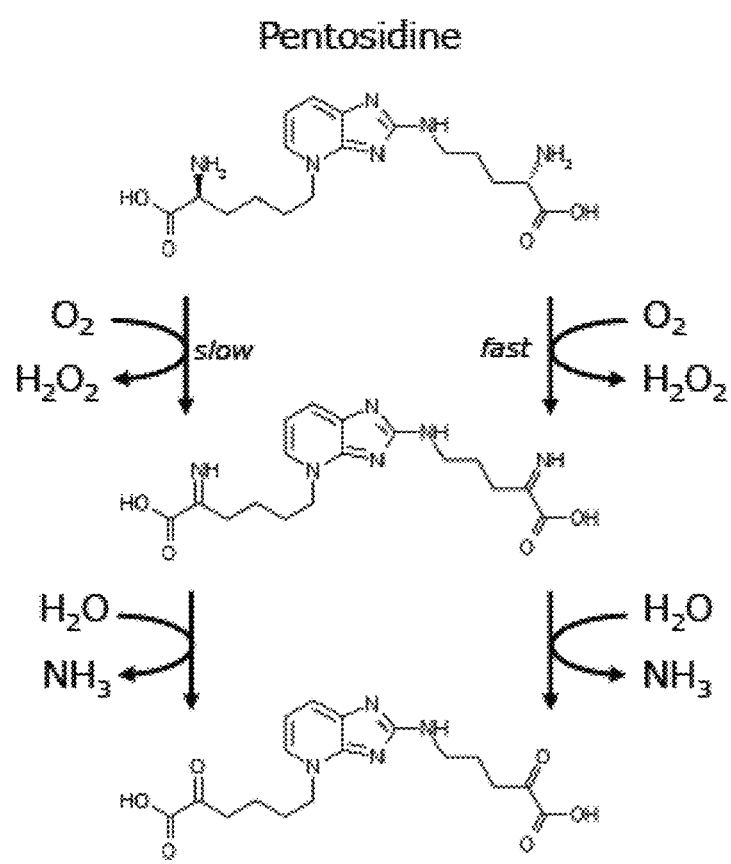
FIG. 5 illustrates a putative mechanism of a reaction in which pentosidine oxidase degrades pentosidine. This drawing illustrates a state where each amino group of lysine and arginine constituting pentosidine is oxidatively deaminated to generate hydrogen peroxide and ammonia.

Examples of the reaction product to be measured in the step (B) include hydrogen peroxide, ammonia and a deaminated product of pentosidine. The amount of hydrogen peroxide of the reaction product can be measured by, for example, a peroxidase reaction. The amount of ammonia of the reaction product can be measured by, for example, an indophenol method, a method using a Nessler reagent or a method for measuring a NADH amount by an enzyme that uses ammonia as a substrate, such as glutamate dehydrogenase or NAD synthase. The term "deaminated product" as used herein means, for example, a product in which one of or both of amino groups of lysine and arginine constituting pentosidine are removed to be substituted with oxygen, and at least one terminal is keto acid. An example of such a deaminated product is shown in FIG. 5. An example of the substance consumed in a reaction to be measured in the step (B) includes oxygen. The amount of oxygen reduced through the enzymatic reaction can be measured, for example, by using an oxygen electrode, or can be colorimetrically determined through oxidation of a manganese ion by oxygen according to the Winkler method.

In another aspect, the present invention provides a kit including pentosidine oxidase. The kit of the present invention can be used for detecting a reaction product or a substance consumed in a reaction between pentosidine and pentosidine oxidase. The kit of the present invention may further include at least one of a reaction buffer solution, a reagent for detecting a reaction product such as a hydrogen peroxide detection reagent, an ammonia detection reagent or a detection reagent for a deaminated product of pentosidine, and a reagent for detecting a substance consumed in the reaction such as an oxygen detection reagent. The kit of the present invention can be used as an ex vivo diagnostic drug as well, and can be suitably used for diagnosis of a disease related to pentosidine or a product resulting from the reaction between pentosidine and pentosidine oxidase, such as diabetes or nephropathy.

Examples of the hydrogen peroxide detection reagent include 10-(carboxymethylaminocarbonyl)-3,7-bis(dimethylamino)-phenothiazine (DA-67) and N-(carboxymethylaminocarbonyl)-4,4'-bis(dimethylamino)-diphenylamine (DA-64), with which hydrogen peroxide can be highly sensitively detected as well as known colorimetric reagents such as a Trinder's reagent. Examples of the ammonia detection reagent include a combination of phenol-sodium nitroprusside and an oxidant such as sodium hypochlorite (indophenol method), and a Nessler reagent. An example of the oxygen detection reagent includes a combination of a manganese ion, sodium hydroxide and sulfuric acid.

The detection of a reaction product utilizing a color reaction can be extremely simple and inexpensively performed as compared with an immunochemical method and an instrumental analysis method. For the detection of a reaction product or a substance consumed in a reaction, however, known quantitative/qualitative methods other than the method using a detection reagent may be appropriately employed. For example, instead of a detection reagent for hydrogen peroxide or ammonia, a device such as an enzyme sensor equipped with an exclusive detection electrode can be used for the detection.

The method for detecting a reaction product or a substance consumed in a reaction can be employed for a method for detecting, and further for a method for diagnosing a disease directly or indirectly related to pentosidine, a reaction product or a substance consumed in a reaction.

Hereinafter, the present invention will be described in more detail with reference to examples. It should be noted that the present invention is not limited to these examples, and can be practiced in various forms as long as the problems of the present invention can be solved.

EXAMPLES (Example 1) Methods for Culturing *Sarocladium* Sp. and Preparing Enzyme Solution Used Media
MEA medium: Malt extract agar (manufactured by Oxoid) was dissolved in distilled water in 50 g/L.
YMG medium: yeast extract 0.4%, malt extract 1%, glucose 0.4%, pH 5.5
Culture of Strain
*Sarocladium* sp. F10012 stored at −80° C. was applied on an MEA medium, and statically cultured at 24° C. for 7 to 10 days until an adequate amount of hypha was obtained. The hypha thus obtained was inoculated into 250 mL of a YMG medium in a 1 L flask, and was shaking cultured at 30° C. for 3 days.
Preparation of Crude Enzyme Solution
The YMG medium in which the microbial cell had been cultured was filtered using Miracloth (manufactured by Merck Millipore Ltd.) to remove the microbial cell, and a culture supernatant was obtained. A process of concentrating the culture supernatant by using an ultrafiltration membrane (Vivaspin 20-3 k, manufactured by GE Healthcare) and diluting the resultant with a 50 mM potassium phosphate buffer (pH 7.5) was repeated a plurality of times to remove low molecules, and to replace the YMG medium with the potassium phosphate buffer.

Crude Purification of Target Enzyme
A crude enzyme solution obtained after the buffer replacement was fractionated using an ion exchange chromatography column (HiTrap Q Sepharose Fast Flow 1 mL, manufactured by GE Healthcare). Specific procedures were as follows.

First, the crude enzyme solution was loaded onto a column equilibrated with the 50 mM potassium phosphate buffer (pH 7.5) to cause the enzyme to adsorb onto the column. Thereafter, the column was washed with 5 mL of the potassium phosphate buffer to elute non-adsorbed protein.

Thereafter, 5 mL each of potassium phosphate buffers respectively containing 0.25 M, 0.5 M, 0.75 M and 1.0 M sodium chloride dissolved therein was passed through the column to elute the protein having been adsorbed onto the column.

A solution eluted from the column when the crude enzyme solution was loaded was designated as "Flow through", a solution eluted in washing with the buffer was designated as "Start buffer", and solutions eluted with the buffers containing sodium chloride were designated respectively as "Elution 1", "Elution 2", "Elution 3" and "Elution 4", and these solutions were collected in different vessels.

(Example 2) Method for Measuring Pentosidine Oxidase Activity

Activity Measurement of Crudely Purified Enzyme Solution
A solution eluted from an ion exchange chromatography column was used as a sample for measuring activity. 50 µL of the sample was mixed with 25 µL of a 100 mM potassium phosphate buffer (pH 8.0) containing 4 mM pentosidine (manufactured by Peptide Institute Inc.) dissolved therein, and 25 µL of an oxidase colorimetric reagent (4 U/mL peroxidase (manufactured by TOYOBO Co., Ltd.), 1.8 mM 4-aminoantipyrine (manufactured by Fluka), 2 mM TOOS (manufactured by DOJINDO LABORATORIES)), and the resultant mixture was reacted at room temperature.

For the reaction, a 96-well microwell plate (manufactured by Nunc) was used. A blank was obtained by adding a 100 mM potassium phosphate buffer (pH 8.0) instead of the substrate solution. Absorbances at 555 nm of the reaction solution and the blank solution were measured, and intensity of enzyme activity was evaluated based on a difference (ΔOD) between these absorbances.

Substrate Dose-Dependence Test
The pentosidine oxidase activity of the crudely purified enzyme solution was measured by using the substrate at various concentrations to evaluate transition of the activity against the concentration of the substrate. The concentrations of the substrate solutions used were 0.13 mM, 0.25 mM, 0.5 mM, 1.0 mM, 2.0 mM and 4.0 mM.

Thermal Inactivation Test
The crudely purified enzyme solution was heat treated at 80° C. for 1 hour to modify the protein. The pentosidine oxidase activity of the sample thus heat-treated was measured in the same manner as in the activity measurement method described above, and compared with the activity of the sample before the heat treatment.

Figure 2:
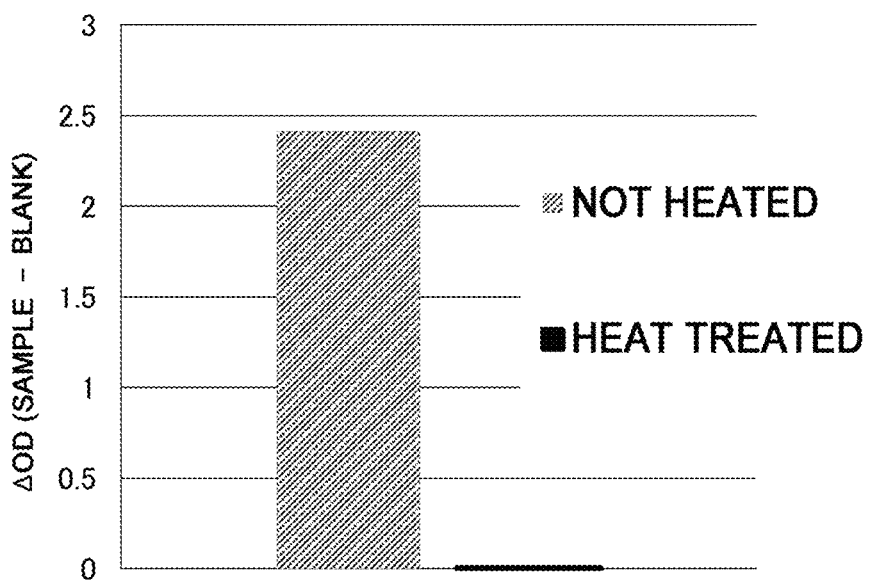
FIG. 2 illustrates a result of a thermal inactivation test of the crudely purified enzyme solution (Elution 1). This result is obtained by analyzing inactivation of enzyme activity through a heat treatment, and corresponds to data obtained 20 minutes after the start of a reaction.

(Example 3) Analysis of Pentosidine Oxidase Activity of *Sarocladium* sp. Enzyme Solution A sample obtained by fractionating a culture supernatant of *Sarocladium* sp. using an ion exchange chromatography column was analyzed for reactivity with pentosidine. As a result, it was found to have strong activity against Elution 1 eluted with the potassium phosphate buffer containing 0.25 M sodium chloride, which suggested that pentosidine oxidase was contained therein. Elution 1 was subjected to a substrate dose-dependence test (FIG. 1) and a thermal inactivation test (FIG. 2). It was revealed that the enzyme activity increased dependently on the substrate concentration, and was completely inactivated by a heat treatment. As a result, it was found that the pentosidine oxidase activity of Elution 1 is derived from the enzyme.

(Example 4) Sequencing of Pentosidine Oxidase Derived from *Sarocladium* Sp.

On the basis of the above-described results and the whole genome sequence information of *Sarocladium* sp., two genes (SEQ ID NOS: 1 and 3) were predicted as pentosidine oxidase and their amino acid sequences (SEQ ID NOS: 2 and 4) were specified.

(Example 5) Heterologous Expression, in *Aspergillus sojae*, of Pentosidine Oxidase Derived from *Sarocladium* sp.

For analyzing the enzyme activity of the two pentosidine oxidases specified as described above, heterologous expression was performed by using *Aspergillus sojae* as a host.

Preparation of Expression Vector

Nucleotide sequences as set forth in SEQ ID NOS: 5 and 6 were obtained by artificial gene synthesis. These sequences were obtained based on the amino acid sequences of SEQ ID NOS: 2 and 4, respectively, with codon modification performed for expressing in *Aspergillus* fungi.

As expression cassettes for expressing each of the pentosidine oxidase genes (penox1 and penox2) of SEQ ID NOS: 5 and 6, a promoter sequence Ptef (748 upstream bps of the tef1 gene, SEQ ID NO: 7) of the translational elongation factor gene tef1 was used as a promoter, and a terminal sequence Talp (800 downstream bps of the alp gene, SEQ ID NO: 8) of the alkali protease gene alp was used as a terminator.

Besides, as a selection marker, a transformation marker gene pyrG3 (1,487 bps including 56 upstream bps, 896 coding region bps and 535 downstream bps, SEQ ID NO: 9) complementing uracil/uridine requirement and enabling multicopy introduction of gene was used (see Japanese Patent Laid-Open No. 2018-068292). The Ptef, Talp and pyrG3 were obtained by PCR using the genomic DNA of *Aspergillus sojae* (NRRC4239) as a template.

Next, for ligating these DNAs, In-Fusion HD Cloning Kit (manufactured by Clontech Laboratories, Inc.) was used. For example, in ligating the Ptef with the penox1 and the Talp, the DNA fragments were amplified by the PCR using a reverse primer of SEQ ID NO: 10 for the Ptef, and a forward primer of SEQ ID NO: 11 for the Talp. At this point, in the reverse primer of SEQ ID NO: 10 used for amplifying the Ptef, a sequence of 15 bps complementary to the 5' terminal sequence of the penox1 gene (SEQ ID NO: 5) was added at the 5' terminal, and in the forward primer of SEQ ID NO: 11 used for amplifying the Talp, a sequence of 15 bps homologous to the 3' terminal sequence of the penox1 gene (SEQ ID NO: 5) was added at the 5' terminal. Therefore, the Ptef, the penox1 gene and the talp can be ligated through the In-fusion reaction. In this manner, expression vectors p19-pG3-penox1 and p19-pG3-penox2 in which Ptef-penox1-Talp-pyrG3 and Ptef-penox2-Talp-pyrG3 obtained by successively ligating the Ptef, the penox1 gene or the penox2 gene, the Talp and the pyrG3 were respectively inserted into a multicloning site of the pUC19 plasmid were prepared.

Preparation and Culture of *Aspergillus* Strain for Gene Expression

The transformation plasmids p19-pG3-penox1 and p19-pG3-penox2 obtained as described above were used to transform a pyrG gene disruptant strain of *Aspergillus sojae* (a strain in which 48 upstream bp, 896 coding region bp and 240 downstream bp of the pyrG gene were deleted) by the protoplast PEG method. As a result, nine As-penox1 strains and six As-penox2 strains of *Aspergillus sojae* transformants in each of which penox1 or penox2 expression cassette was multicopy inserted were obtained.

Each of the As-penox1 and As-penox2 strains of *Aspergillus sojae* transformants thus obtained was inoculated into 15 mL of a PPY liquid medium (2% (w/v) Pinedex, 1% (w/v) polypeptone, 0.5% (w/v) yeast extract, 0.5% (w/v) monopotassium dihydrogen phosphate, 0.05% (w/v) magnesium sulfate•heptahydrate) held in a 50 mL Erlenmeyer flask, and was shaking cultured at 30° C. for 4 to 5 days.

Preparation of Hypha Extract

A culture fluid obtained from each of the As-penox1 strains and As-penox2 strains was filtered using Miracloth (manufactured by Merck Millipore Ltd.) to remove a culture supernatant, and thus, a microbial cell was obtained. The microbial cell was resuspended in 15 mL of a 10 mM potassium phosphate buffer (pH 7.5), and then disrupted using Micro Smash MS-100R (manufactured by Tomy Seiko Co., Ltd.). The microbial cell disruption liquid thus obtained was centrifuged at 15,000 rpm for 15 minutes to collect a supernatant as a crude enzyme solution.

Measurement of L-Arginine Oxidation Activity of Hypha Extract

200 µL of each crude enzyme solution was mixed with a 380 µL of 150 mM potassium phosphate buffer solution (pH 7.0) in which 7.1 U/mL peroxidase, 0.70 mM 4-aminoantipyrine and 0.79 mM TOOS were dissolved. The resultant mixture was incubated at 37° C. for 5 minutes, and 20 µL of a 60 mM L-arginine solution was added thereto, followed by stirring, and reacting at 37° C. for 5 minutes. A change over time of $A_{555}$ during the reaction was measured using a spectrophotometer (U-3900, manufactured by Hitachi High-Tech Science Corporation). A control experiment was performed by adding 20 µL of ion-exchanged water instead of 20 µL of the 60 mM L-arginine solution. An amount of the enzyme generating 1 µmol of hydrogen peroxide per minute at 37° C. was defined as one unit (U), and the activity was calculated in accordance with the following equation:

$$\text{Activity }(U/mL) = \{(\Delta As - \Delta A0) \times 0.6 \times df\}/(39.2 \times 0.5 \times 0.2)$$

$\Delta As$: change of $A_{555}$ per minute of reaction solution
$\Delta A0$: change of $A_{555}$ per minute of control experiment
39.2: millimolar absorbance coefficient ($mM^{-1} \cdot cm^{-1}$) of quinoneimine pigment generated through reaction
0.5: molar number of quinoneimine pigment generated by 1 mol of hydrogen peroxide 0.6: volume (mL) of whole reaction solution
df: dilution factor
0.2: volume (mL) of enzyme solution The L-arginine oxidation activity of the crude enzyme solutions of As-penox1 strains and As-penox2 strains were respectively 0.009 U/mL (As-penox1-15 strain) and 5.1 U/mL (As-penox2-16 strain) at a maximum.

(Example 6) Purification of Intracellular Recombinant Penox2

The crude enzyme solution of the As-penox2-16 strain was subjected to the buffer replacement with a 10 mM potassium phosphate buffer (pH 7.5), and then fractionated using an anion exchange chromatography column (HiScreen CaptoQ, manufactured by GE Healthcare). First, the crude enzyme solution was loaded onto a column equilibrated with a 10 mM potassium phosphate buffer (pH 7.5) to cause the enzyme to adsorb onto the column. Thereafter, the column was washed with a 10 mM potassium phosphate buffer (pH 7.5) to elute non-adsorbed protein. Thereafter, a sodium chloride concentration in a 10 mM potassium phosphate buffer (pH 7.5) was linearly increased from 0 mM to 40 mM to elute the protein having been adsorbed onto the column. A fraction exhibiting L-arginine oxidation activity was analyzed by SDS-PAGE, and a fraction not containing contaminant protein was collected as purified PenOX2. The purified PenOX2 solution thus collected was concentrated by using Amicon Ultra-15 Ultracel-30 k (manufactured by Millipore) to obtain a concentrate with the L-arginine oxidation activity of 24 U/mL. This concentrate was used in a pentosidine quantitative test.

(Example 7) Pentosidine Quantitative Test

The following reagents were prepared to measure pentosidine by using Bio Majesty JCA-BM1650 (manufactured by JEOL Ltd.).
(Sample: Pentosidine Solution)
0.2 µM, 0.4 µM, 0.6 µM, 1.0 µM, 2.0 µM or 4.0 µM pentosidine solution
(First Reagent: Leuco Pigment, Peroxidase Solution)
120 mM potassium phosphate buffer (pH 7.0)
0.2 mM DA-67 (10-(carboxymethylaminocarbonyl)-3,7-bis(dimethylamino)phenothiazine, sodium salt) (manufactured by Wako Pure Chemical Industries, Ltd.)
3.0 U/mL peroxidase
(Second Reagent: PenOX2 Solution)
120 mM potassium phosphate buffer (pH 7.0)
24 U/mL PenOX2

25 µL of the sample was added to 50 µL of the first reagent, and the resultant was incubated at 37° C. for 5 minutes. Then, 25 µL of the second reagent was added thereto to allow a pentosidine oxidation reaction owing to PenOX2 and a detection reaction for hydrogen peroxide generated through the reaction to proceed at 37° C. for 5 minutes.

Figure 3:
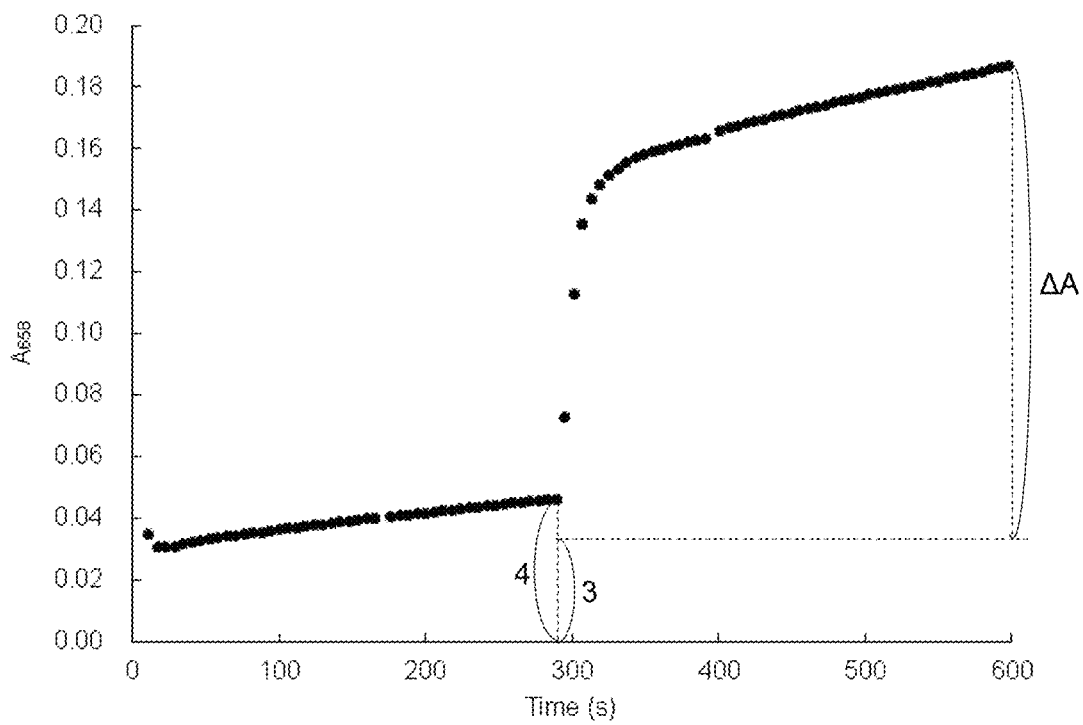
FIG. 3 illustrates a result of measurement of a concentration of hydrogen peroxide generated through a reaction between pentosidine and pentosidine oxidase. The concentration of hydrogen peroxide was measured based on an absorbance at 658 nm.

In the detection reaction for hydrogen peroxide, simultaneously with consumption of peroxidase, DA-67 is oxidized into methylene blue to present the color, and the absorbance ($A_{658}$) is increased. As an example, the relationship between the elapsed time after the mixture of the sample (4.0 µM pentosidine solution) and the first reagent and the absorbance ($A_{658}$) is shown in FIG. 3. It was confirmed that $A_{658}$ increased immediately after the addition of the second reagent containing PenOX2.

Subsequently, an $A_{658}$ increment (AA) caused by the oxidation of pentosidine was calculated in accordance with the following equation:

$$\Delta A = (\text{absorbance 5 min after addition of second reagent}) - (\text{absorbance immediately before addition of second reagent} \times 0.75)$$

(A concentration of the composition in the reaction solution is reduced by 0.75 times (75/100 times) through the addition of the second reagent, and hence, the value obtained by multiplying, by 0.75, the absorbance immediately before the addition of the second reagent was regarded as the absorbance immediately after the addition of the second reagent.)

Figure 4:
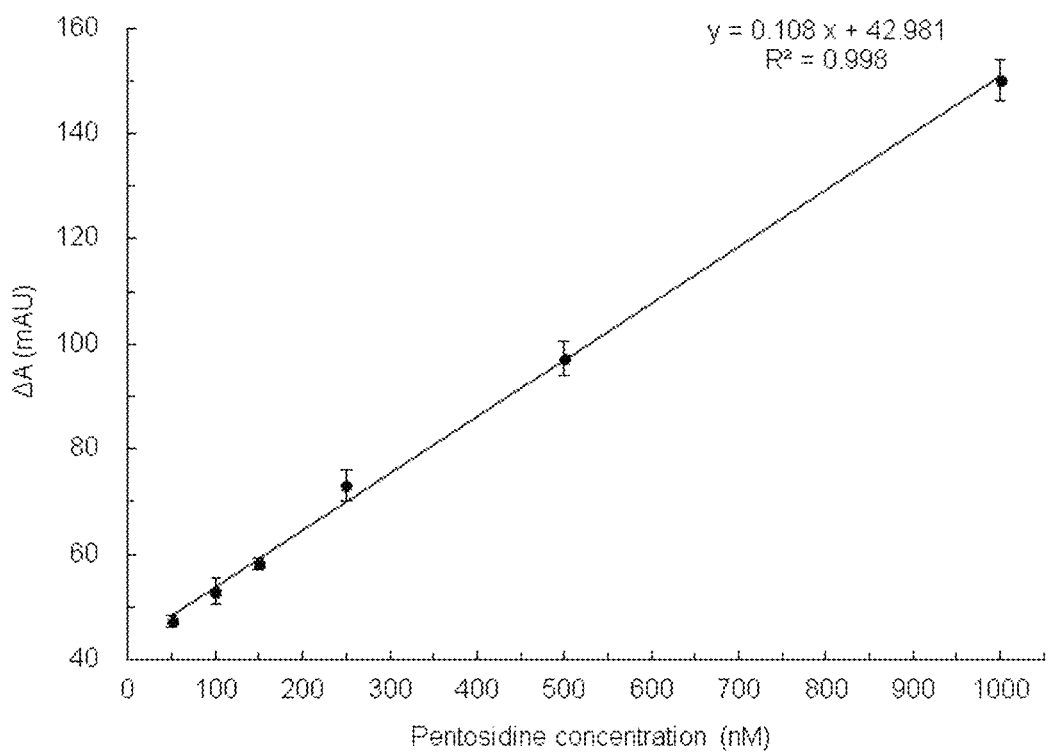
FIG. 4 illustrates the relationship between a final pentosidine concentration and an increment of $A_{658}$ (ΔA) caused by oxidation of pentosidine.

There was correlation between a final pentosidine concentration and ΔA (FIG. 4). Accordingly, it was revealed that PenOX2 exhibits the pentosidine oxidation activity and can be used for quantitative determination of pentosidine. Although a result is not described herein, PenOX1 also similarly exhibited pentosidine oxidation activity.

(Example 8) Purification of Extracellular Recombinant Penox2

A hypha culture fluid of the As-penox2 strain was filtered by using Miracloth (manufactured by Merck Millipore Ltd.), and a hypha culture supernatant was collected. 75 mL of the hypha culture supernatant thus obtained was filtered through a syringe filter having a pore size of 0.2 µm, and then, the resultant was concentrated using an ultrafiltration membrane (Amicon Ultra 15-30 kD, manufactured by Merck). To the concentrate thus obtained, ammonium sulfate was gradually added to obtain saturation of 70%, the resultant was allowed to stand at 4° C. for 2 hours, and then centrifuged (15,000 rpm, 4° C., 5 minutes) to precipitate redundant protein, and a supernatant was collected. The collected supernatant was concentrated using an ultrafiltration membrane (Amicon Ultra 0.5-30 kD, manufactured by Merck).

A potassium phosphate buffer (pH 7.5) and ammonium sulfate were added thereto to final concentrations of 50 mM and 2 M respectively, and the resultant was fractionated using a hydrophobic interaction chromatography column (HiTrap Butyl Fast Flow 1 mL, manufactured by GE Healthcare). Specific procedures were as follows.

First, the crude enzyme solution was loaded onto a column equilibrated with a 50 mM potassium phosphate buffer (pH 7.5) containing 2 M ammonium sulfate to cause the enzyme to adsorb onto the column. Thereafter, the column was washed with 10 mL of a 50 mM potassium phosphate buffer (pH 7.5) containing 2 M ammonium sulfate to elute non-adsorbed protein.

Thereafter, 5 mL each of 50 mM potassium phosphate buffers (pH 7.5) respectively containing 1.5 M, 1.3 M and 1.15 M ammonium sulfate, and further 10 mL of a 50 mM potassium phosphate buffer (pH 7.5) containing 1 M ammonium sulfate, and 5 mL of a 50 mM potassium phosphate buffer (pH 7.5) not containing ammonium sulfate were successively passed through the column to elute the protein having been adsorbed onto the column.

A solution eluted from the column when the crude enzyme solution was loaded was designated as "Flow through 1", a solution eluted in washing with the buffer containing 2 M ammonium sulfate was designated as "Elution 1", and solutions eluted with the buffers respectively containing 1.5 M, 1.3 M, 1.15 M and 1 M ammonium sulfate were designated respectively as "Elution 2", "Elution 3", "Elution 4" and "Elution 5", a solution eluted with the buffer not containing ammonium sulfate was designated as "Elution 6", and these solutions were collected in different vessels.

Each of samples obtained by the fractionation was analyzed for the reactivity with pentosidine. As a result, Elution 5 eluted with the potassium phosphate buffer containing 1 M ammonium sulfate was found to have strong activity, and was suggested to contain pentosidine oxidase (PenOX2). Elution 5 was concentrated by using an ultrafiltration membrane (Amicon Ultra 15-30 kD, manufactured by Merck), subjected to buffer replacement with a 50 mM potassium phosphate buffer (pH 7.5) not containing ammonium sulfate, and concentrated again by using an ultrafiltration membrane (Amicon Ultra 15-30 kD, manufactured by Merck). The resultant was fractionated by using an ion exchange chromatography column (HiTrap Q Sepharose Fast Flow 1 mL, manufactured by GE Healthcare). Specific procedures were as follows.

First, the crude enzyme solution was loaded onto a column equilibrated with a 50 mM potassium phosphate buffer (pH 7.5) to cause the enzyme to adsorb onto the column, and thereafter, the column was washed with 5 mL of a 50 mM potassium phosphate buffer (pH 7.5) to elute non-adsorbed protein.

Thereafter, 1 mL of a solution obtained by dissolving 0.1 M sodium chloride in a 50 mM potassium phosphate buffer (pH 7.5) (five times), 1 mL of a solution obtained by dissolving 0.175 M sodium chloride in the buffer (five times), and 5 mL of a solution obtained by dissolving 1 M sodium chloride in the buffer (once) were successively passed through the column to elute the protein having been adsorbed onto the column.

A solution eluted from the column when the crude enzyme solution was loaded was designated as "Flow through 2", a solution eluted in washing with the buffer was designated as "Elution 7", and solutions eluted with the buffers containing sodium chloride were designated respectively as "Elution 8-1", "Elution 8-2", "Elution 8-3", "Elution 8-4", "Elution 8-5", "Elution 9-1", "Elution 9-2", "Elution 9-3", "Elution 9-4", "Elution 9-5" and "Elution 10", and these solutions were collected in different vessels.

Each of samples obtained by the fractionation was analyzed for the reactivity with pentosidine. As a result, Elution 9-1 and Elution 9-2 eluted with the potassium phosphate buffers containing 0.175 M sodium chloride were found to have strong activity, and were suggested to contain pentosidine oxidase. When a mixture of equivalent amounts of the active fractions Elution 9-1 and Elution 9-2 was analyzed by SDS-PAGE, a substantially single band was obtained (molecular weight: about 80,000). The active fraction thus obtained was used for determining the following physicochemical properties.

(Example 9) Physicochemical Properties of PenOX2 Produced from *Aspergillus sojae* Transformant As-penox2 Strain In order to determine physicochemical properties of PenOX2, the following methods for measuring the enzyme activity were employed.

600 µL of an arbitrary buffer, 400 µL of deionized water solution in which 3.99 U/mL peroxidase, 1.8 mM 4-aminoantipyrine and 2 mM TOOS were dissolved, and 150 µL of deionized water were incubated at an arbitrary temperature for 10 minutes. Then, 50 µL of the enzyme solution having been stored on ice and 400 µL of a solution of 4 mM pentosidine dissolved in a 100 mM potassium phosphate buffer (pH 8.0) having been incubated at an arbitrary temperature for 10 minutes were added thereto, followed by stirring and reacting at an arbitrary temperature for 3 minutes. A change over time of $A_{555}$ during the reaction was measured using a spectrophotometer (U-3900, manufactured by Hitachi High-Tech Science Corporation). An elapsed time from the start of the measurement of 20 seconds to 60 seconds—$A_{555}$ change was regarded as an activity value.

Besides, an amount of the enzyme generating 1 µmol of hydrogen peroxide per minute at 37° C. was defined as one unite (U), and the activity was calculated in accordance with the following equation.

$$\text{Activity } (U/mL) = \{(\Delta As - \Delta A0) \times 1.6 \times df\}/(39.2 \times 0.5 \times 0.05)$$

$\Delta As$: change of $A_{555}$ per minute of reaction solution
$\Delta A0$: change of $A_{555}$ per minute of control experiment
1.6: volume (mL) of whole reaction solution
df: dilution factor
39.2: millimolar absorbance coefficient ($mM^{-1}$-cm-1) of quinoneimine pigment generated through reaction
0.5: molar number of quinoneimine pigment generated by 1 mol of hydrogen peroxide
0.05: volume (mL) of enzyme solution The physicochemical properties of penox2 were as follows:

(a) Range of Optimum pH

A 50 mM citric acid-100 mM potassium phosphate buffer (pH 4.0 to 7.5, a final concentration), a potassium phosphate buffer (pH 6.5 to 8.0, a final concentration of 100 mM), and a glycine buffer (pH 8.0 to 11.0, a final concentration of 100 mM) were prepared, and these were used to perform an enzymatic reaction at respective pH at a temperature of 37° C. Results are shown in FIG. 7. PenOX2 exhibited the highest activity at pH 7.5. Besides, it exhibited, also at pH 6.5 to 8.0, 70% or more of an activity value obtained in the potassium phosphate buffer of around pH 7.5. Therefore, it was determined that the optimum pH of PenOX2 is pH 6.5 to 8.0, and that the most suitable optimum pH is pH 7.5.

(b) Range of Optimum Temperature

Figure 8:
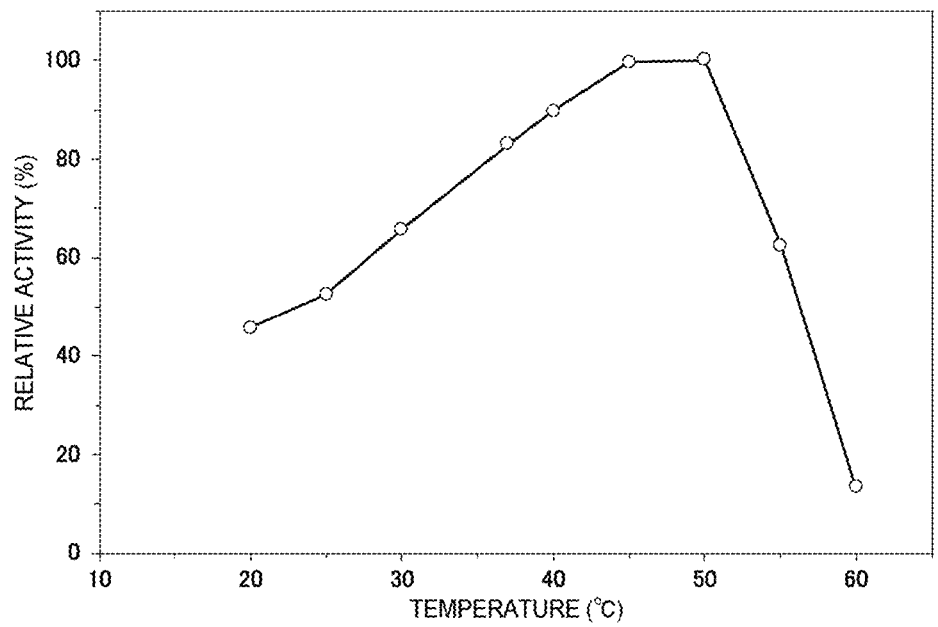
FIG. 8 illustrates a range of optimum temperature of PenOX2.

A potassium phosphate buffer (pH 7.5) having a final concentration of 50 mM was used to perform the activity measurement of PenOX2 at various temperatures. Results are shown in FIG. 8. The highest activity was obtained around 50° C., and a temperature range for attaining 80% or more of this highest activity was 37° C. to 50° C. Therefore, it was determined that the range of the optimum temperature of PenOX2 is 37° C. to 50° C.

(c) Thermal Stability

Figure 9:
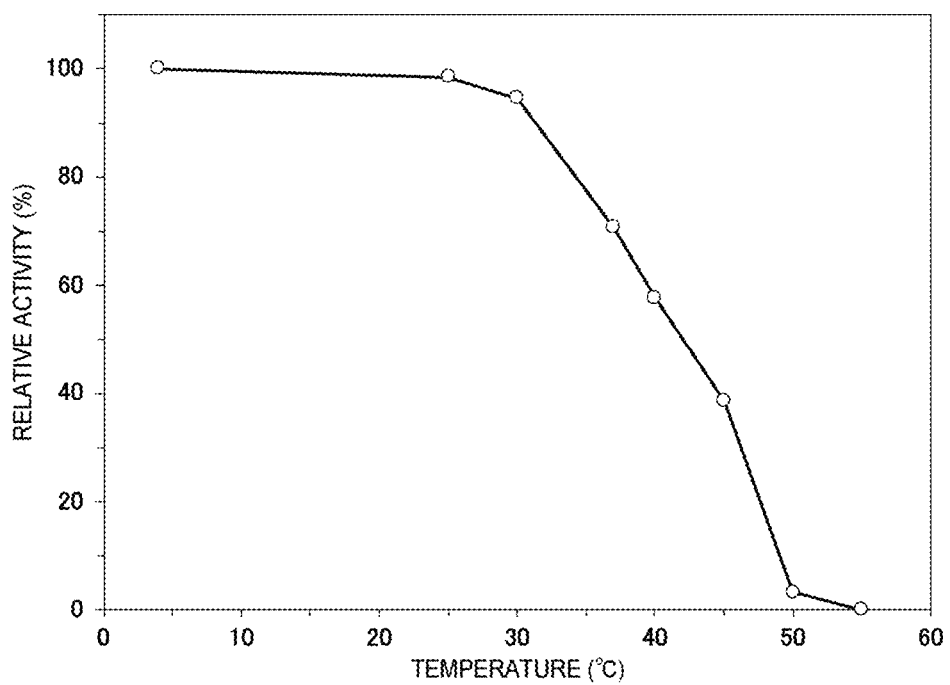
FIG. 9 illustrates a range of thermal stability of PenOX2.

Residual activity obtained when the enzyme solution was treated for 10 minutes at respective temperatures was evaluated by performing the activity measurement described above by using a potassium phosphate buffer (final pH in the activity measurement: pH 7.5, final concentration of 100 mM) at 37° C. Results of thermal stability are shown in FIG. 9. It was found that PenOX2 was stable up to about 30° C.

(d) Range of Stable pH

Figure 10:
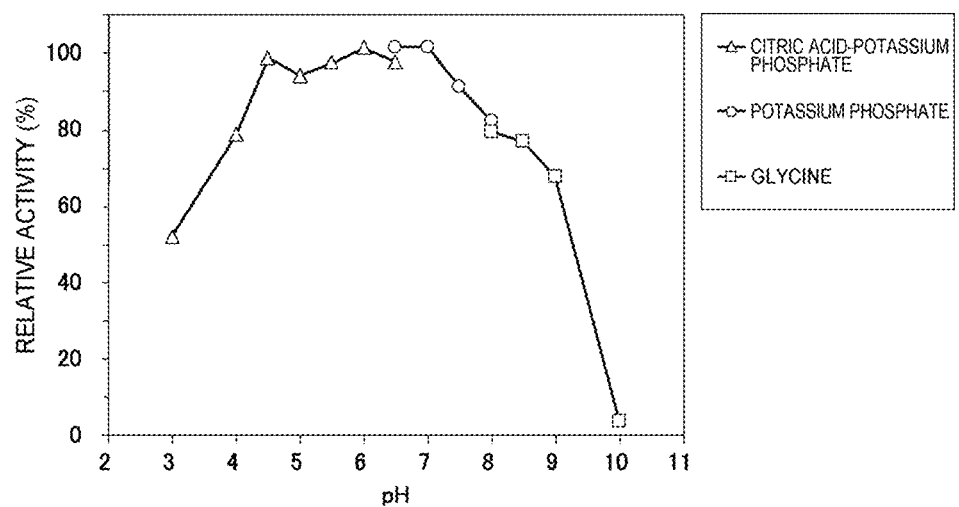
FIG. 10 illustrates a range of stable pH of PenOX2.

Treatments were performed respectively using, as a buffer solution, a 100 mM citric acid-200 mM potassium phosphate buffer (pH 3.0 to 6.5), a 200 mM potassium phosphate buffer (pH 6.5 to 8.0) and a 200 mM glycine buffer (pH 8.0 to 10.0) at respective pH and at 25° C. for 20 hours, and then, residual activity of PenOX2 was measured. Results are shown in FIG. 10. At pH range of pH 4.5 to 7.5, 90% or more of the activity of PenOX2 having been stored at 4° C. was exhibited. At pH range of pH 4.0 to 9.0, 60% or more of the activity of PenOX2 having been stored at 4° C. was exhibited.

(e) Activity Value against Pentosidine

The above-described activity measurement method was employed to perform activity measurement using a potassium phosphate buffer (final pH in the activity measurement: pH 7.5, final concentration of 50 mM) at 37° C., and an activity value (U/mL) was obtained by using the aforementioned equation. It was found that the activity value was 7.8 U/mL and specific activity was 29.1 U/mg (Bradford method).

(f) Km Value for Pentosidine

Figure 11:
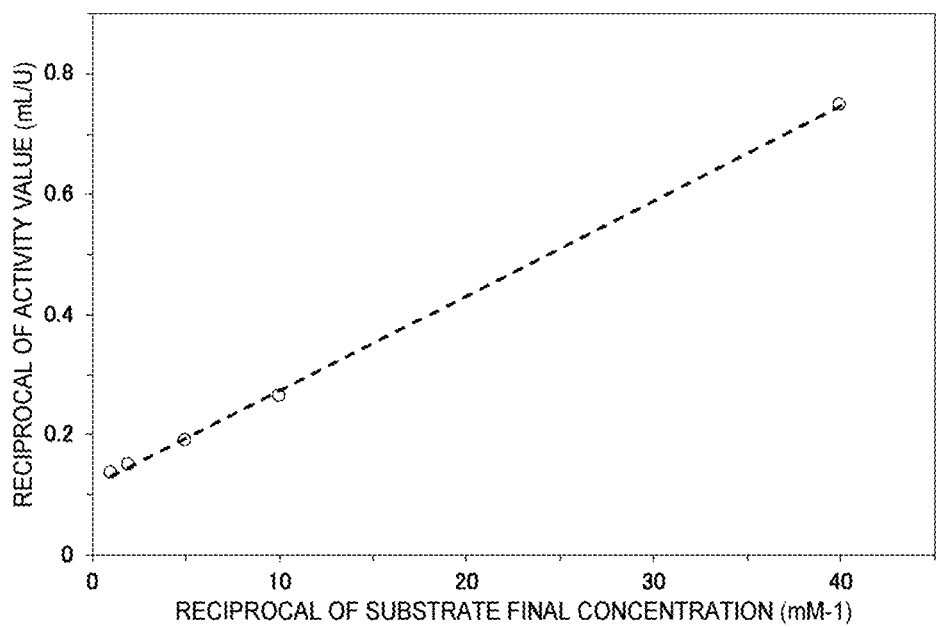
FIG. 11 illustrates a Km value of PenOX2 against pentosidine.

The above-described activity measurement method was employed to perform activity measurement using a potassium phosphate buffer (pH 7.5, final concentration of 50 mM) at 37° C. with varying concentration of the substrate of pentosidine, and a Michaelis constant (Km) was obtained based on the Lineweaver-Burk plot. Results are shown in FIG. 11. It was found that the Km value for pentosidine is 0.14 mM.

(g) Molecular Weight

Figure 12:
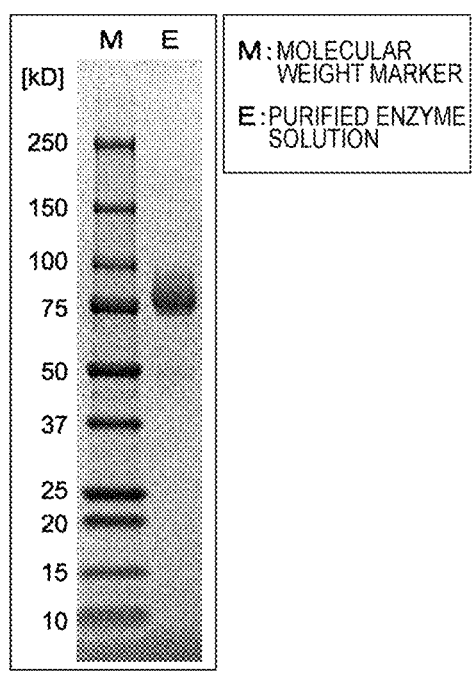
FIG. 12 illustrates a molecular weight of PenOX2.

A molecular weight was obtained by SDS-PAGE performed according to the Laemmli method. As an electrophoresis gel, Mini-PROTEAN TGX Stain-Free Precast Gels 4-20% (manufactured by Bio-Rad Laboratories, Inc.) was used, and as a molecular weight marker, Precision Plus Protein All Blue Prestained Protein Standard was used. Results are shown in FIG. 12. It was found that the molecular weight of PenOX2 is about 80,000.

(Example 10) Measurement of Pentosidine Oxidase Activity of Enzyme Having Sequence Homology with PenOX1 and PenOX2

As described above, both PenOX1 and PenOX2 had the pentosidine oxidase activity. An amino acid sequence concordance rate was confirmed by using a BLAST program, and it was found that the amino acid sequence homology therebetween was 38.2%. Subsequently, the following three enzymes were purchased, and the above-described activity measurement method was employed for confirming their pentosidine oxidase activity using a potassium phosphate buffer (pH 7.5, final concentration of 100 mM) at 37° C. The amino acid sequence homologies with PenOX1 and PenOX2 and the pentosidine oxidase activities of these enzymes were as follows.

(a) Amino Acid Oxidase Type VI Derived from *Crotalus adamanteus* (Manufactured by Merck) (SEQ ID NO: 12)

Molecular Weight: 130,000

The amino acid sequence homologies of this enzyme with PenOX1 and PenOX2 were 26.8% and 23.5%, respectively. The enzyme was diluted with deionized water to an enzyme concentration of 1 mg/mL (biuret method) to be used for the activity measurement. This enzyme had pentosidine oxidase activity of 0.555 (U/mL) and specific activity of 0.555 (U/mg).

(b) Amino Acid Oxidase Type I Derived from *Crotalus atrox* (Manufactured by Merck) (SEQ ID NO: 13)

Molecular Weight: 59,000 (value calculated based on amino acid sequence)

The amino acid sequence homologies of this enzyme with PenOX1 and PenOX2 were 26.3% and 23.4%, respectively. 1 mg of a powder of this enzyme was dissolved in 1 mL of deionized water to be used for the activity measurement. This enzyme had pentosidine oxidase activity of 0.022 (U/mL) and specific activity, as a reference value, of 0.022 (U/mg).

(c) Lysine Oxidase Derived from *Trichoderma viride* (Manufactured by Merck) (SEQ ID NO: 14)

Molecular Weight: 116,000

The amino acid sequence homologies of this enzyme with PenOX1 and PenOX2 were 24.0% and 23.3%, respectively. 1 mg of a powder of this enzyme was dissolved in 1 mL of deionized water to be used for the activity measurement. This enzyme had pentosidine oxidase activity of 0.063 (U/mL) and specific activity, as a reference value, of 0.063 (U/mg). The sequence homologies among the enzymes used in this example are shown in the following table.

The invention claimed is:

1. A method for measuring pentosidine, comprising:
contacting a protein with a specimen, wherein the protein is selected from the group consisting of:
   (a) a protein consisting of an amino acid sequence as set forth in SEQ ID NO: 2 or 4;
   (b) a protein encoded by a gene consisting of a nucleotide sequence as set forth in SEQ ID NO: 1, 3, 5 or 6;
   (c) a protein comprising at least 90% sequence identity to SEQ ID NO: 2 or 4; and
   (d) a protein encoded by a gene comprising at least 90% sequence identity to SEQ ID NO: 1, 3, 5 or 6; and
detecting a change caused by the contact.

2. The method according to claim 1, wherein a change in an amount of oxygen, hydrogen peroxide or ammonia is detected in the detecting step.

3. The method according to claim 1, wherein the protein is extracted from a filamentous fungus.

4. The method according to claim 1, wherein the protein has an optimum pH of about 6.5 to 8.0.

5. The method according to claim 1, wherein the protein has an optimum temperature of 37 to 50° C.

6. The method according to claim 1, wherein 90% or more of the activity of the protein is retained after storage at 30° C. for 10 minutes.

7. A recombinant vector comprising the gene selected from the group consisting of:
   (a) a gene encoding a protein consisting of an amino acid sequence as set forth in SEQ ID NO: 2 or 4;
   (b) a gene consisting of a nucleotide sequence as set forth in SEQ ID NO: 1, 3, 5 or 6;
   (c) a gene encoding a protein comprising at least 90% sequence identity to SEQ ID NO: 2 or 4; and
   (d) a gene comprising at least 90% sequence identity to SEQ ID NO: 1, 3, 5 or 6.

8. A transformant comprising the vector according to claim 7.

* * * * *

SEQUENCE LISTING

<160> NUMBER OF SEQ ID NOS: 14

<210> SEQ ID NO 1
<211> LENGTH: 2487
<212> TYPE: DNA
<213> ORGANISM: Unknown
<220> FEATURE:
<223> OTHER INFORMATION: Sarocladium sp.

<400> SEQUENCE: 1

```
atgaagtctc ccagtctggc cgtggccggc cttcttcttg gctcgagttc cttaagccat      60
gctacccagc ttcgtattga gacgaggaaa tcgctcaact ctcgtatcgc caacgtccac     120
attgatgttg acgctccagt cgctcaccaa gttgtcttca catatggccc ttgtgattcg     180
gagagccaag agaacgctca ccatgtcatt gctcaaagcc aaaagctaga gggcaggaaa     240
ccccatcgat tgatctggac tatgcccaag gatcttcacc cggatgactg catctctgcg     300
tggggtgaat caggagacct cctcggtcgc agtgtccctc aaaaggtcgc gcacaaggag     360
atgaggagac gcaagagaga tgatagcgac tactccatcc ctatgaacag ctcgagtggc     420
atcgacgttt atggcccttg gttcgatggt gtagctctcc tcgagaagag cgacaatcac     480
```

| | |
|---|---|
| aatgtggacg tcgaagccgc caaggccaag gagattgcta tcgtcggggc tgggatggct | 540 |
| ggtctgacca cgtacttcat cctcagtgaa gctggactca gcaacctgac gatcctggag | 600 |
| gcaagtggtc gtcttggagg ccgcgtacgc accgaatatc tctccggagg acccagggac | 660 |
| cattcctatg ccgagatggg ccctatgcgg atcccatacc aggctcgttt tggagacaag | 720 |
| gcatacaaca tctcggatca agcaatattc ttccgacttg tggagaaggt gaacgagcgg | 780 |
| aacaagaagc ttgaaacaca caaggacctc atcaacctga tcccgttcat ccagtccagt | 840 |
| ccgaatgggc tcgcttatta tcaaggtaac aagctggaga atgggctgcc gccaacgcag | 900 |
| gcagatgttg ctgcagatcc agcactgggg aatgaatccc ctgagatccc tgaatctgca | 960 |
| caagaattgg ctgctcagct tcagagagca ttgcctaacg ctgaattcct tgagctaatg | 1020 |
| gccacaaact tctggcaagc ccatgccgaa ttcctcggta tgttgcttca gctcaccacc | 1080 |
| ccgtatagcc agggctctca aaccctcata gaggatgcca ctaaaatgaa atgcgaatgt | 1140 |
| agagaatcag gtccagctg gcctgcctgg cgatcagtgg tctgagtttg ctttcctggt | 1200 |
| gaactacctc aacgcgaccg tcttcgatgc caacgcagtc actggtggtt atgactggca | 1260 |
| cagcagcctt gacagggtac gtgacgctga agaagatctc gtggttgcat cattaatccc | 1320 |
| acggtctccc tagttgtact acactatgct cttcggaggc gggggcagtt tcaagacgat | 1380 |
| tgatggaggc aagtcaaaat gagcgttgcg ggcacctgga cgagaactga cagagctcgc | 1440 |
| tcgtaggcat gaacttgctc cccaacgctt tccatcccct agttgacgat atcacgaagt | 1500 |
| tcaatgcaaa agtagagaag gttcagctcg atgagaagac ttcccgcctg aagctgcatt | 1560 |
| ggcgcgcgaa ctacactgat ccggagctcg agtcgcagtc atttgactac gccattctgt | 1620 |
| cacctaccat gccagcagta cagaagttgc gccttccagg taggtcctgc gcaatctctc | 1680 |
| gttgctttgc ggaccatagc tttcaatgtc acaggtctac ccttcgctat gcgcaacgcc | 1740 |
| gtcgactcca tgccttacgc ctctgcgtgc aaagtcgccc tcgaataccg cactcggttc | 1800 |
| tgggaaaagt tcgacaaccc catctacggc tcctgttcca ccagcaccga cattcccggt | 1860 |
| attggatccg tgtgctaccc atcttccaac atcaacggca gcggcccagc ttccctcctt | 1920 |
| gcgagctacg agattggcag gccttacggc gcagagtggg ctggcattcc tgaggagcag | 1980 |
| catgtgcagt atgtgattga cgcaatgatt gatatccacg gcgaggttgc acgacgagag | 2040 |
| tttaccggga aatgcaagag aaagtgttgg gctctggacg agttctcaaa cgggggttgg | 2100 |
| gcttcaccga ccgtgggtaa tcatgagacg tatctgccat cgttttcga cccacagc | 2160 |
| catgtgagtg ctccgacatt tgacctcttg tgcgaggaat gagggacttg ttgaccttgt | 2220 |
| tccagatgat attcgtgggt gagcatacct cctatacaca cgcatggatc gcctctgcga | 2280 |
| tcgaatctgc agtccgaggc agcgtgcagc tgctcttggg tatgtttcgc gttcttgcaa | 2340 |
| atcgtgcaga tgtgcttctg acattacttt gccacagagc ttggccttat agacgaggcg | 2400 |
| aaggatgtcg taaacacgtg gatggcacga tggatcagtg ttgtaagtga cctaagcaaa | 2460 |
| gccgtggtgt ctggagcgtc agcgtag | 2487 |

<210> SEQ ID NO 2
<211> LENGTH: 689
<212> TYPE: PRT
<213> ORGANISM: Unknown
<220> FEATURE:
<223> OTHER INFORMATION: Sarocladium sp.

<400> SEQUENCE: 2

Met Lys Ser Pro Ser Leu Ala Val Ala Gly Leu Leu Leu Gly Ser Ser

-continued

```
1               5                   10                  15
Ser Leu Ser His Ala Thr Gln Leu Arg Ile Glu Thr Arg Lys Ser Leu
                20                  25                  30
Asn Ser Arg Ile Ala Asn Val His Ile Asp Val Asp Ala Pro Val Ala
                35                  40                  45
His Gln Val Val Phe Thr Tyr Gly Pro Cys Asp Ser Glu Ser Gln Glu
        50                  55                  60
Asn Ala His His Val Ile Ala Gln Ser Gln Lys Leu Glu Gly Arg Lys
 65                 70                  75                  80
Pro His Arg Leu Ile Trp Thr Met Pro Lys Asp Leu His Pro Asp Asp
                    85                  90                  95
Cys Ile Ser Ala Trp Gly Glu Ser Gly Asp Leu Leu Gly Arg Ser Val
                100                 105                 110
Pro Gln Lys Val Ala His Lys Glu Met Arg Arg Arg Lys Arg Asp Asp
                115                 120                 125
Ser Asp Tyr Ser Ile Pro Met Asn Ser Ser Ser Gly Ile Asp Val Tyr
        130                 135                 140
Gly Pro Trp Phe Asp Gly Val Ala Leu Leu Glu Lys Ser Asp Asn His
145                 150                 155                 160
Asn Val Asp Val Glu Ala Ala Lys Ala Lys Glu Ile Ala Ile Val Gly
                165                 170                 175
Ala Gly Met Ala Gly Leu Thr Thr Tyr Phe Ile Leu Ser Glu Ala Gly
                180                 185                 190
Leu Ser Asn Leu Thr Ile Leu Glu Ala Ser Gly Arg Leu Gly Gly Arg
                195                 200                 205
Val Arg Thr Glu Tyr Leu Ser Gly Gly Pro Arg Asp His Ser Tyr Ala
        210                 215                 220
Glu Met Gly Pro Met Arg Ile Pro Tyr Gln Ala Arg Phe Gly Asp Lys
225                 230                 235                 240
Ala Tyr Asn Ile Ser Asp Gln Ala Ile Phe Phe Arg Leu Val Glu Lys
                245                 250                 255
Val Asn Glu Arg Asn Lys Lys Leu Gly Asn Thr Lys Asp Leu Ile Asn
                260                 265                 270
Leu Ile Pro Phe Ile Gln Ser Pro Asn Gly Leu Ala Tyr Tyr Gln
        275                 280                 285
Gly Asn Lys Leu Glu Asn Gly Leu Pro Pro Thr Gln Ala Asp Val Ala
        290                 295                 300
Ala Asp Pro Ala Leu Gly Asn Glu Ser Pro Glu Ile Pro Glu Ser Ala
305                 310                 315                 320
Gln Glu Leu Ala Ala Gln Leu Gln Arg Ala Leu Pro Asn Ala Glu Phe
                325                 330                 335
Leu Glu Leu Met Ala Thr Asn Phe Trp Gln Ala His Ala Glu Phe Leu
                340                 345                 350
Glu Asn Gln Gly Pro Ala Gly Leu Pro Gly Asp Gln Trp Ser Glu Phe
                355                 360                 365
Ala Phe Leu Val Asn Tyr Leu Asn Ala Thr Val Phe Asp Ala Asn Ala
        370                 375                 380
Val Thr Gly Gly Tyr Asp Trp His Ser Ser Leu Asp Arg Ser Ser Leu
385                 390                 395                 400
Val Gly Met Asn Leu Leu Pro Asn Ala Phe His Pro Leu Val Asp Asp
                405                 410                 415
Ile Thr Lys Phe Asn Ala Lys Val Glu Lys Val Gln Leu Asp Glu Lys
                420                 425                 430
```

```
Thr Ser Arg Leu Lys Leu His Trp Arg Ala Asn Tyr Thr Asp Pro Glu
        435                 440                 445
Leu Glu Ser Gln Ser Phe Asp Tyr Ala Ile Leu Ser Pro Thr Met Pro
    450                 455                 460
Ala Val Gln Lys Leu Arg Leu Pro Gly Leu Pro Phe Ala Met Arg Asn
465                 470                 475                 480
Ala Val Asp Ser Met Pro Tyr Ala Ser Ala Cys Lys Val Ala Leu Glu
                485                 490                 495
Tyr Arg Thr Arg Phe Trp Glu Lys Phe Asp Asn Pro Ile Tyr Gly Ser
            500                 505                 510
Cys Ser Thr Ser Thr Asp Ile Pro Gly Ile Gly Ser Val Cys Tyr Pro
        515                 520                 525
Ser Ser Asn Ile Asn Gly Ser Gly Pro Ala Ser Leu Leu Ala Ser Tyr
    530                 535                 540
Glu Ile Gly Arg Pro Tyr Gly Ala Glu Trp Ala Gly Ile Pro Glu Glu
545                 550                 555                 560
Gln His Val Gln Tyr Val Ile Asp Ala Met Ile Asp Ile His Gly Glu
                565                 570                 575
Val Ala Arg Arg Glu Phe Thr Gly Lys Cys Lys Arg Lys Cys Trp Ala
            580                 585                 590
Leu Asp Glu Phe Ser Asn Gly Gly Trp Ala Ser Pro Thr Val Gly Asn
        595                 600                 605
His Glu Thr Tyr Leu Pro Ser Phe Phe Glu Thr His Ser His Met Ile
    610                 615                 620
Phe Val Gly Glu His Thr Ser Tyr Thr His Ala Trp Ile Ala Ser Ala
625                 630                 635                 640
Ile Glu Ser Ala Val Arg Gly Ser Val Gln Leu Leu Glu Leu Gly
                645                 650                 655
Leu Ile Asp Glu Ala Lys Asp Val Val Asn Thr Trp Met Ala Arg Trp
        660                 665                 670
Ile Ser Val Val Ser Asp Leu Ser Lys Ala Val Val Ser Gly Ala Ser
    675                 680                 685
Ala

<210> SEQ ID NO 3
<211> LENGTH: 2086
<212> TYPE: DNA
<213> ORGANISM: Unknown
<220> FEATURE:
<223> OTHER INFORMATION: Sarocladium sp.

<400> SEQUENCE: 3
atgttcactc ccaaagcttg gatccctctg ttggccttga gccgcgaggt cttctccaat    60
cctacttctg catcccattc catctctttc cacggtctcc ttggcgtctc ttcggagtca   120
gtccacaaca tccacctcac ttatggcgat gccttccac atggagactt ccgtgttgtc    180
tttggagact gcggtatgac cagtgaggat gaacttcatc acgaggttgc atctctctcc   240
acgaagatgg agtctgctcc tgatcgtttg gtctggcttg tgccaaagga tgtccgcgag   300
aatggttgtc ttcacgcttt ctcggagggc gtcctcctcg gtcggtctga gcctgtcgct   360
ttcacagagc cactccggaa gcgcgagtct ctctctgaga ttggtgactc cgatggcctc   420
tggttcagcg gaatccgcta tctgcagtca agcaacctga catccgtcaa ggccgccgaa   480
gctaaggaaa agaagattgg catcgttggc ggtggcattt ccggtctgat gacgagtctg   540
```

```
ctcctgactt ccgtcggcat gaccaactgg cacatcattg aggcgactga gcgtgtcgga    600
ggccgcatcc gcaccaagta tatgaatgga actagtcccg atgactacca gtaccaggag    660
atggggccca tgaggttccc cgttgaggtc aaatacaacg acaccaacga dacgctgccc    720
attcaggatc acaagatggt cttccagctg gctgaagtct tgaacgagat gaacggcaac    780
gacacagatc tcgctgtcaa gttcattccc tggacccaga caatccgaa cactcccgcc    840 aactctcgag gataccgcct ccctgatggc cgcatcccta ccgcggccca aatcgcccag    900
aaccccagca tcttgccggc agctgccaac gcgtcagacc ccaagatgc ggaacttggc    960 aaggagtcct tggagcgtct cagtgacctt accccgagc ggatgcgcaa catctccgcc   1020
aacatcttca aggcgcaccg agatgccatt gaccgcggct gtttcactg gtctgaggca   1080 gcctatctcc ggtaccagct gggccttgac gacgatactg tggacttcgt ggctgcctcc   1140
gacaactatc ccatgttccc tgactggtgg cacgcggtct acttcgcggc cacgaagtgg   1200
ctcacgatcg acaagggcct cgattcgctg tccagggctt ttgtacccca cgtcaaggac   1260
aagatcacgt acggtcgcaa gattgaagcc atgcaatgga atgagtcaac atccaagatc   1320
tcactgtcat ggagggagag ccctcttgcg gcggcgaagt ccgatgagta cgactatgct   1380
gtcgtcgcgg tgccgttctc caaggttcgt ctgtggaagc ggccggctta ctccaacctc   1440
ttgacgaggg ctattggcaa gctgaactac gagcaggcct gcaaagtgag caccccctca   1500
tccgcccgaa gagtgactag aatactaatc cctccaaaag gttgctctgc tctacgagac   1560
acgcttctgg gagcaccagg agatccccat cttttggaggc tgtggctcgg ttgatatccc   1620
gggtattggt ggcgtgtgct acccatcata cgagatcaac tccacgaggc ctggcgtgat   1680
tctctcttcc tacattaccg gcacagaagc cagatccgtg gtagccctga gcgaggaaga   1740
tcacgtcgcc atggtgcagc gtgccatggt cgaagtccac ggccctatgg cggatgagca   1800
gtggaccggg atttacgacc gtctgtgctg ggaggtggat gagaacgcgg ccggaggctg   1860
ggcttcgccg acagttggcc agcaggagct gttcatcccg cgtaccaca agacggagct   1920 caacaccatc ttcatcggag agcacacgag catcacgcac gggtggatct tctcggccct   1980
ggaatcgtcg gtcaggggca cgacgcagtt gctgctcgat cttggtctag tggatgaggc   2040
gaagcagatt gttgagactt ggatggcgag gtggatcacc gtttga              2086
```

<210> SEQ ID NO 4
<211> LENGTH: 676
<212> TYPE: PRT
<213> ORGANISM: Unknown
<220> FEATURE:
<223> OTHER INFORMATION: Sarocladium sp.

<400> SEQUENCE: 4

```
Met Phe Thr Pro Lys Ala Trp Ile Pro Leu Leu Ala Leu Ser Arg Glu
1               5                   10                  15

Val Phe Ser Asn Pro Thr Ser Ala Ser His Ser Ile Ser Phe His Gly
            20                  25                  30

Leu Leu Gly Val Ser Ser Glu Ser Val His Asn Ile His Leu Thr Tyr
        35                  40                  45

Gly Asp Ala Phe Pro His Gly Asp Phe Arg Val Phe Gly Asp Cys
    50                  55                  60

Gly Met Thr Ser Glu Asp Glu Leu His His Glu Val Ala Ser Leu Ser
65                  70                  75                  80

Thr Lys Met Glu Ser Ala Pro Asp Arg Leu Val Trp Leu Val Pro Lys
                85                  90                  95
```

```
Asp Val Arg Glu Asn Gly Cys Leu His Ala Phe Ser Glu Gly Val Leu
            100                 105                 110

Leu Gly Arg Ser Glu Pro Val Ala Phe Thr Glu Pro Leu Arg Lys Arg
            115                 120                 125

Glu Ser Leu Ser Glu Ile Gly Asp Ser Asp Gly Leu Trp Phe Ser Gly
            130                 135                 140

Ile Arg Tyr Leu Gln Ser Ser Asn Leu Thr Ser Val Lys Ala Ala Glu
145                 150                 155                 160

Ala Lys Glu Lys Lys Ile Gly Ile Val Gly Gly Ile Ser Gly Leu
                165                 170                 175

Met Thr Ser Leu Leu Thr Ser Val Gly Met Thr Asn Trp His Ile
            180                 185                 190

Ile Glu Ala Thr Glu Arg Val Gly Gly Arg Ile Arg Thr Lys Tyr Met
            195                 200                 205

Asn Gly Thr Ser Pro Asp Asp Tyr Gln Tyr Gln Glu Met Gly Pro Met
            210                 215                 220

Arg Phe Pro Val Glu Val Lys Tyr Asn Asp Thr Asn Glu Thr Leu Pro
225                 230                 235                 240

Ile Gln Asp His Lys Met Val Phe Gln Leu Ala Glu Val Leu Asn Glu
                245                 250                 255

Met Asn Gly Asn Asp Thr Asp Leu Ala Val Lys Phe Ile Pro Trp Thr
            260                 265                 270

Gln Asn Asn Pro Asn Thr Pro Ala Asn Ser Arg Gly Tyr Arg Leu Pro
            275                 280                 285

Asp Gly Arg Ile Pro Thr Ala Ala Gln Ile Ala Gln Asn Pro Ser Ile
            290                 295                 300

Leu Pro Ala Ala Ala Asn Ala Ser Asp Pro Gln Asp Ala Glu Leu Gly
305                 310                 315                 320

Lys Glu Ser Leu Glu Arg Leu Ser Asp Leu Thr Pro Glu Arg Met Arg
                325                 330                 335

Asn Ile Ser Ala Asn Ile Phe Lys Ala His Arg Asp Ala Ile Asp Arg
            340                 345                 350

Gly Leu Phe His Trp Ser Glu Ala Ala Tyr Leu Arg Tyr Gln Leu Gly
            355                 360                 365

Leu Asp Asp Asp Thr Val Asp Phe Val Ala Ala Ser Asp Asn Tyr Pro
370                 375                 380

Met Phe Pro Asp Trp Trp His Ala Val Tyr Phe Ala Ala Thr Lys Trp
385                 390                 395                 400

Leu Thr Ile Asp Lys Gly Leu Asp Ser Leu Ser Arg Ala Phe Val Pro
                405                 410                 415

His Val Lys Asp Lys Ile Thr Tyr Gly Arg Lys Ile Glu Ala Met Gln
            420                 425                 430

Trp Asn Glu Ser Thr Ser Lys Ile Ser Leu Ser Trp Arg Glu Ser Pro
            435                 440                 445

Leu Ala Ala Ala Lys Ser Asp Glu Tyr Asp Tyr Ala Val Val Ala Val
            450                 455                 460

Pro Phe Ser Lys Val Arg Leu Trp Lys Arg Pro Ala Tyr Ser Asn Leu
465                 470                 475                 480

Leu Thr Arg Ala Ile Gly Lys Leu Asn Tyr Glu Gln Ala Cys Lys Val
                485                 490                 495

Ala Leu Leu Tyr Glu Thr Arg Phe Trp Glu His Gln Glu Ile Pro Ile
            500                 505                 510
```

| | | | | | | | | | | | |
|---|---|---|---|---|---|---|---|---|---|---|---|
|Phe|Gly|Gly|Cys|Gly|Ser|Val|Asp|Ile|Pro|Gly|Ile|Gly|Val|Cys|
| |515| | | |520| | | |525| | | | | |

Phe Gly Gly Cys Gly Ser Val Asp Ile Pro Gly Ile Gly Val Cys
            515                 520                 525

Tyr Pro Ser Tyr Glu Ile Asn Ser Thr Arg Pro Gly Val Ile Leu Ser
        530                 535                 540

Ser Tyr Ile Thr Gly Thr Glu Ala Arg Ser Val Val Ala Leu Ser Glu
545                 550                 555                 560

Glu Asp His Val Ala Met Val Gln Arg Ala Met Val Glu Val His Gly
            565                 570                 575

Pro Met Ala Asp Glu Gln Trp Thr Gly Ile Tyr Asp Arg Leu Cys Trp
        580                 585                 590

Glu Val Asp Glu Asn Ala Ala Gly Gly Trp Ala Ser Pro Thr Val Gly
            595                 600                 605

Gln Gln Glu Leu Phe Ile Pro Ala Tyr His Lys Thr Glu Leu Asn Thr
        610                 615                 620

Ile Phe Ile Gly Glu His Thr Ser Ile Thr His Gly Trp Ile Phe Ser
625                 630                 635                 640

Ala Leu Glu Ser Ser Val Arg Gly Thr Thr Gln Leu Leu Leu Asp Leu
            645                 650                 655

Gly Leu Val Asp Glu Ala Lys Gln Ile Val Glu Thr Trp Met Ala Arg
        660                 665                 670

Trp Ile Thr Val
        675

<210> SEQ ID NO 5
<211> LENGTH: 2070
<212> TYPE: DNA
<213> ORGANISM: Unknown
<220> FEATURE:
<223> OTHER INFORMATION: Sarocladium sp.

<400> SEQUENCE: 5

```
atgaagtctc catctctggc tgtggctggt ctcctgcttg gatcctctag cctctcgcat      60
gccacccagc tgcgcatcga aactcgtaag tcgctcaact cccgcatcgc taatgtgcat     120
atcgatgttg acgcccctgt cgctcaccag gtcgtgttca cctacggtcc ctgcgattcc     180
gagtctcagg aaaacgccca tcacgttatc gctcagtcgc agaagctcga gggacggaag     240
cctcatcgcc tgatctggac tatgcctaag gatcttcacc ccgatgactg tatctctgcc     300
tggggagaat ctggtgactt gctcggccgg tccgtgccac agaaggttgc tcataaggag     360
atgcgccgtc ggaagcgcga tgactctgac tacagcatcc caatgaactc gtcctctgga     420
atcgatgtgt atggcccgtg gttcgacggt gttgccctgc ttgagaagtc cgataaccac     480
aatgttgacg tcgaagccgc taaggccaag gagatcgcta tcgtcggagc cggcatggct     540
ggccttacca cttatttcat cttgtcggaa gccggtcttt ccaacttgac catcctcgaa     600
gcttctggac gcctgggcgg tcgtgtgcgc actgaatacc tttctggagg ccccgtgat     660
cacagctatg ccgagatggg ccctatgcgt atcccctacc aggcccggtt cggtgataag     720
gcttataata tcagcgacca ggctatcttc ttccgcctcg tcgagaaggt taacgagcgc     780
aataagaagc ttggaaacac caaggacctg atcaatctta ccctttcat ccagagctcg     840
cccaacggac tggcctacta tcagggcaac aagttggaaa atggtctccc tcccactcaa     900
gctgatgtgg ctgctgaccc agctctcggt aatgagtcgc agaaattcc tgagtctgct     960
caagaattgg ctgctcagct tcagcgtgct tgccgaacg ctgaattcct tgagttgatg    1020
gccaccaatt tctggcaggc ccatgctgaa ttcttggaga accagggtcc agctggactc    1080
```

```
ccgggcgatc agtggtctga gttcgccttc ctcgtcaact acctgaatgc taccgttttc    1140
gacgccaatg ctgtcactgg tggatatgat tggcattcct ctcttgaccg cagctcgttg    1200
gttggcatga acttgctccc aaatgccttc cacccgttgg tcgatgacat caccaagttc    1260
aacgctaagg tcgaaaaggt gcagctcgat gagaagacct ctcgcctcaa gctgcactgg    1320
cgtgccaatt acactgatcc agagttggaa agccagtcgt tcgactatgc catcctcagc    1380
cctaccatgc ccgctgtcca gaagcttcgt ttgccaggct tgccgttcgc catgcggaac    1440
gctgtcgact ctatgcctta cgccagcgct tgcaaggtgg ctcttgaata tcgtactcgg    1500
ttctgggaga agttcgataa tcccatctac ggttcctgct ctaccagcac tgacatccca    1560
ggtatcggat ccgtttgtta tccgtcctct aacatcaatg ctccggtcc ggcctctctg      1620 cttgctagct acgaaattgg acgtccttat ggtgctgagt gggctggcat ccccgaggaa    1680
cagcatgttc agtacgtcat cgatgccatg atcgacatcc acggagaagt cgctcgccgt    1740
gagttcaccg gcaagtgcaa gcgtaagtgt tgggccctgg atgagttctc taacggcggt    1800
tgggcctctc caaccgtggg aaatcatgaa acttaccttc cgtcgttctt cgagactcat    1860
tcccacatga tcttcgttgg cgaacatacc tcgtatactc acgcctggat cgcctcggct    1920
atcgagtccg ctgtccgtgg ttccgtgcag ttgctcctgg aactcggact gatcgatgag    1980
gccaaggacg ttgtcaacac ctggatggct cggtggatct cggtggtttc cgatctgtct    2040
aaggccgtcg tgagcggtgc ctcggcttga                                    2070

<210> SEQ ID NO 6
<211> LENGTH: 2031
<212> TYPE: DNA
<213> ORGANISM: Artificial Sequence
<220> FEATURE:
<223> OTHER INFORMATION: codon-modified g4462 (penox1)

<400> SEQUENCE: 6
atgttcactc ctaaggcttg gattccactc ctggctctga ccgcgaggt cttctcgaac        60 cctacctctg cctctcatag catctcgttc cacggacttt tgggcgtctc ctctgaatct     120
gtgcataata tccaccttac ctacggtgac gctttccccc atggagattt ccgtgtcgtg     180
ttcggtgact gcggaatgac ttctgaggat gaactgcatc acgaggtcgc ctcccttcct     240
accaagatgg aaagcgctcc agaccgcctc gtgtggctgg ttccgaagga tgtgcgtgag    300
aacggatgtt tgcacgcctt ctctgaaggc gttctcctgg gtcggagcga gcctgtcgct    360
ttcactgaac ccttgcgcaa gcgtgagagc ctctcggaaa tcgagactc tgatggcctg      420 tggttcagcg gcatccgcta tctgcagagc tcgaatctta cctctgtcaa ggccgctgag    480
gccaaggaaa agaagatcgg tatcgtgggc ggtggaatct ccggactat gacctctctt      540 ttgctcacta gcgtgggtat gaccaactgg catatcatcg aggctaccga acgcgttggc    600
ggtcggatcc gcactaagta catgaatgga accagccctg atgactacca gtatcaggag    660
atgggcccta tgcgtttccc cgtcgaggtg aagtataacg acaccaatga aactctcccc    720
atccaggatc acaagatggt gttccagttg gccgaggttc tcaacgaaat gaacggcaat    780
gacactgatt tggctgtcaa gttcatccca tggactcaga caatcctaa caccctgcc     840 aatagccgcg gctaccgtct cccagacggt cgtatcccga ccgccgctca gatcgctcag    900
aacccatcta ttttgcctgc tgctgctaat gcttctgacc cacaggatgc tgagcttggc    960
aaggagtcgc ttgaacggtt gtccgatctc actccggaac gtatgcggaa catctcggcc   1020
aatatcttca aggcccatcg tgacgctatc gatcggggtc tgttccactg gtccgaggct   1080
```

```
gcctaccttc gctatcagct cggactggat gacgataccg tcgacttcgt ggctgcctcc    1140
gataactacc caatgttccc ggactggtgg catgctgtgt atttcgctgc caccaagtgg    1200
ctgactatcg acaagggcct ggattccctt tctcgggcct tcgttccaca cgtcaaggat    1260
aagatcactt acggtcgcaa gatcgaggct atgcagtgga atgaaagcac ctcgaagatc    1320
tccctttcct ggcgtgagtc gccgctcgct gctgctaagt ccgacgaata cgattatgcc    1380
gttgtcgctg ttccattctc taaggtccgt ctgtggaagc gtcctgccta ttccaacctg    1440
cttactcgcg ctatcggcaa gcttaattac gagcaggcct gcaaggtggc tttgctctat    1500
gaaacccgtt tctgggagca tcaggaaatc ccaatcttcg gaggctgcgg atcggtggat    1560
atccctggca tcggtggagt ttgttacccc tcttatgaga tcaacagcac ccgtccggga    1620
gttatcttgt cctcttatat caccggcact gaagcccgt cggtggttgc tctctccgag    1680
gaagaccatg tggccatggt tcagcgggct atggttgagg tccacggtcc catggccgat    1740
gaacagtgga ctggaatcta cgaccgcctc tgttgggaag tcgatgaaaa tgctgctggc    1800
ggttgggctt ctcctactgt tggacagcag gagttgttca tccccgctta tcacaagacc    1860
gagctcaata ctatcttcat cggcgaacat acctcgatca ctcacggttg gatcttctcc    1920
gccctggaga gctcggttcg tggcaccact cagctgcttt tggaccttgg tttggtcgat    1980
gaggccaagc agatcgtgga aacttggatg gctcggtgga tcaccgtctg a             2031

<210> SEQ ID NO 7
<211> LENGTH: 748
<212> TYPE: DNA
<213> ORGANISM: Artificial Sequence
<220> FEATURE:
<223> OTHER INFORMATION: Ptef

<400> SEQUENCE: 7
tgtggaccag acaggcgcca ctcggccggg ccacaactgc ttgggttttg accgggagcg      60
gaccaattaa ggactcgaac gaccgcgggg ttcaaatgca aacaagtaca acacgcagca    120
aacgaagcag cccaccactg cgttgatgcc cagtttgtct gtccgaaatc caccggaaag    180
gtggaaacat actatgtaac aatcagaggg aagaaaaatt ttttatcgac gaggcaggat    240
agtgactgat ggtggggtca tggtcgggtc tccgagcgaa agagaaccaa ggaaacaaga    300
tcaacgaggt tggtgtaccc aaaaggccgc agcaacaaga gtcatcgccc aaaagtcaac    360
agtctggaag agactccgcc gtgcagattc tgcgtcggtc ccgcacatgc gtggtggggg    420
cattacccct ccatgtccaa tgataagggc ggcggtcgag ggcttaagcc cgcccactaa    480
ttcgccttct cgcttgcccc tccatataag gattccctc cttcccctcc cacaactttt    540
ttcctctttc tctcttcgtc cgcatcagta cgtatatctt tccccctac ctctttctca    600 ctcttcctcg attcattcca ctcttctcct tactgacatc tgttttgctc agtacctcta    660
cgcgatcagc cgtagtatct gagcaagctt ttttacagaa tctttctagt atcttacaaa    720
gaactacaaa gttcgcacca ccttcaaa                                       748

<210> SEQ ID NO 8
<211> LENGTH: 800
<212> TYPE: DNA
<213> ORGANISM: Artificial Sequence
<220> FEATURE:
<223> OTHER INFORMATION: Talp

<400> SEQUENCE: 8
```

```
gtaccaggag tacattggag agttctacca ttgttgctgg aatacaatga tgattagaaa    60
ccgaagagtg ttatgattcg gacggatata cgcatggcac gcatacagcg tgatacatag   120
gctgtttgct caagaattag gattttatct gaatccatgt acagagttta cttatgttag   180
tagtcaatga aatcttggct ttctaattt gtccgatcta caaggggtag tcgatcacag    240
aacgaactag atgtgcaggg aacgatgatc acccgctctt agcaagacct ctagtagttt   300
tcgaccatag ctttaacgcg aatcatgacc ctactatttt ctagattgca gaccaagtca   360
catgacaatg tcctctttga agtaggatca gtagctgatt agattccggg aaatgaatta   420
gggctggcgt tccaactact ggggagtgcc gatgttgctg tatgaaagat agtaagatta   480
ctagtgcaca gctgtagtaa ttatttactc tagattatat attccaaata ataagtaatc   540
taagatagta gacagtccta tgatatagct ccggggttcga agtcggcaaa agatatgcaa   600
tcacctgtcg ggatgatata tgtatatctg aaataccgac atcaaccatc cagtcggatc   660
agctaaacga agtatcactt ctttcgccac tgccaatcac tacttctatt aaagttcatg   720
ttacagtata agccacaaga cttatctcca gaactaactt gtgcatagga gctctgccga   780
tagccgggtg gttggatcgg                                                800
```

```
<210> SEQ ID NO 9
<211> LENGTH: 1487
<212> TYPE: DNA
<213> ORGANISM: Artificial Sequence
<220> FEATURE:
<223> OTHER INFORMATION: pyrG3

<400> SEQUENCE: 9
```

```
taagtactca tttatacaat agttgcagaa ccccgcgcta cccctccatt gccaacatgt    60
cttccaagtc gcaattgacc tacagcgcac gcgctagcaa gcaccccaat gcgctcgtga   120
agaagctctt cgaggttgcc gaggccaaga aaaccaatgt caccgttttcc gccgacgtga   180 caaccaccaa agagctgctg gatttggctg accgtatgcg caccggggat gccacttaca   240
tatgatctag taatggttaa tggtggaata tataacagga ctcggtccgt acattgccgt   300
gatcaaaact cacatcgata tcctctccga tttcagcgaa gagaccatca tcggtctgaa   360
ggcccttgca gagaagcaca atttcctcat cttcgaagat cgcaagttca tcgatatcgg   420
aaacacagtc caaaagcagt accatggcgg cactctgcgc atctctgagt gggcccacat   480
catcaactgc agtattctgc ccggtgaggg tatcgtcgag gctctggccc agactgcttc   540
ggccgaggac ttcccctatg gctctgagag ggggccttttg atccttgcgg agatgacatc   600
caagggatct ttggctaccg gtcaatatac tacttcttct gttgactatg cccggaagta   660
taagaagttt gtgatgggat tcgtctcgac gcgtcacctg ggcgaggttc agtctgaagt   720
tagctcgcct tcggaggagg aggatttcgt cgtcttcacg acaggtgtca acctctcctc   780
gaagggagac aaactgggac agcaatacca gactcctgag tctgctgttg gacgcggtgc   840
cgactttatc attgctggtc gtggaattta tgctgctcct gatcccgtgg aggcagcgaa   900
gcggtaccag aaagagggat gggatgcata ccagaagcgt gttggtgcgc aataagtagt   960
ggtgaatacg tgctctttt atggcagtat atcgcaagta tgatgcgatt cataaattca   1020
gcagtcgaat tctacgagag aacgatgcta agagatacc tctctatatg aataatatgc   1080
ctgcctcgag atatggacat attcaagatc agagttaagg gtcatgtttc aaaatcacac   1140
caatctccaa catagacgag aattttttacc ggattgtctg aaggtgcagc tggagattgg   1200
tctatttcct aagagtgggg tatcactaat gtacagtcgg tcactatcgt acaaacaatc   1260
```

```
acaattatat acaagatttc ccatcacccc ttactctaac atggcacttt tatccatcga    1320
gtccgagcct agccaccatt tggtgctttc gtagagacca agtataaacc ctgatccgac    1380
agcggccata acgtgttga tagcacaccc tcggaatagt cctctcgggc catctgttcg    1440
tataatctcc cgtacggtat tgatcatcct tttcttctga ggtgcgg                 1487
```

<210> SEQ ID NO 10
<211> LENGTH: 40
<212> TYPE: DNA
<213> ORGANISM: Artificial Sequence
<220> FEATURE:
<223> OTHER INFORMATION: Ptef reverse primer

<400> SEQUENCE: 10

```
agatggagac ttcattttga aggtggtgcg aactttgtag                            40
```

<210> SEQ ID NO 11
<211> LENGTH: 38
<212> TYPE: DNA
<213> ORGANISM: Artificial Sequence
<220> FEATURE:
<223> OTHER INFORMATION: Talp forward primer

<400> SEQUENCE: 11

```
ggtgcctcgg cttgagtacc aggagtacat tggagagt                              38
```

<210> SEQ ID NO 12
<211> LENGTH: 498
<212> TYPE: PRT
<213> ORGANISM: Crotalus adamanteus

<400> SEQUENCE: 12

Ala His Asp Arg Asn Pro Leu Glu Glu Cys Phe Arg Glu Thr Asp Tyr
1               5                   10                  15

Glu Glu Phe Leu Glu Ile Ala Lys Asn Gly Leu Thr Ala Thr Ser Asn
            20                  25                  30

Pro Lys Arg Val Val Ile Val Gly Ala Gly Met Ala Gly Leu Ser Ala
        35                  40                  45

Ala Tyr Val Leu Ala Gly Ala Gly His Gln Val Thr Val Leu Glu Ala
    50                  55                  60

Ser Glu Arg Val Gly Gly Arg Val Arg Thr Tyr Arg Lys Lys Asp Trp
65                  70                  75                  80

Tyr Ala Asn Leu Gly Pro Met Arg Leu Pro Thr Lys His Arg Ile Val
                85                  90                  95

Arg Glu Tyr Ile Lys Lys Phe Asp Leu Lys Leu Asn Glu Phe Ser Gln
            100                 105                 110

Glu Asn Glu Asn Ala Trp Tyr Phe Ile Lys Asn Ile Arg Lys Arg Val
        115                 120                 125

Arg Glu Val Lys Asn Asn Pro Gly Leu Leu Glu Tyr Pro Val Lys Pro
    130                 135                 140

Ser Glu Glu Gly Lys Ser Ala Ala Gln Leu Tyr Val Glu Ser Leu Arg
145                 150                 155                 160

Lys Val Val Glu Glu Leu Arg Ser Thr Asn Cys Lys Tyr Ile Leu Asp
                165                 170                 175

Lys Tyr Asp Thr Tyr Ser Thr Lys Glu Tyr Leu Leu Lys Glu Gly Asn
            180                 185                 190

Leu Ser Pro Gly Ala Val Asp Met Ile Gly Asp Leu Leu Asn Glu Asp
        195                 200                 205

-continued

```
Ser Gly Tyr Tyr Val Ser Phe Ile Glu Ser Leu Lys His Asp Asp Ile
    210                 215                 220
Phe Gly Tyr Glu Lys Arg Phe Asp Glu Ile Val Gly Gly Met Asp Gln
225                 230                 235                 240
Leu Pro Thr Ser Met Tyr Glu Ala Ile Lys Glu Lys Val Gln Val His
                245                 250                 255
Phe Asn Ala Arg Val Ile Glu Ile Gln Gln Asn Asp Arg Glu Ala Thr
            260                 265                 270
Val Thr Tyr Gln Thr Ser Ala Asn Glu Met Ser Ser Val Thr Ala Asp
        275                 280                 285
Tyr Val Ile Val Cys Thr Thr Ser Arg Ala Ala Arg Ile Lys Phe
290                 295                 300
Glu Pro Pro Leu Pro Pro Lys Lys Ala His Ala Leu Arg Ser Val His
305                 310                 315                 320
Tyr Arg Ser Gly Thr Lys Ile Phe Leu Thr Cys Thr Lys Lys Phe Trp
                325                 330                 335
Glu Asp Asp Gly Ile His Gly Gly Lys Ser Thr Thr Asp Leu Pro Ser
            340                 345                 350
Arg Phe Ile Tyr Tyr Pro Asn His Asn Phe Thr Ser Gly Val Gly Val
        355                 360                 365
Ile Ile Ala Tyr Gly Ile Gly Asp Asp Ala Asn Phe Phe Gln Ala Leu
370                 375                 380
Asp Phe Lys Asp Cys Ala Asp Ile Val Ile Asn Asp Leu Ser Leu Ile
385                 390                 395                 400
His Glu Leu Pro Lys Glu Asp Ile Gln Thr Phe Cys His Pro Ser Met
                405                 410                 415
Ile Gln Arg Trp Ser Leu Asp Lys Tyr Ala Met Gly Gly Ile Thr Thr
            420                 425                 430
Phe Thr Pro Tyr Gln Phe Gln His Phe Ser Glu Ala Leu Thr Ala Pro
        435                 440                 445
Phe Lys Arg Ile Tyr Phe Ala Gly Glu Tyr Thr Ala Gln Phe His Gly
    450                 455                 460
Trp Ile Asp Ser Thr Ile Lys Ser Gly Leu Thr Ala Ala Arg Asp Val
465                 470                 475                 480
Asn Arg Ala Ser Glu Asn Pro Ser Gly Ile His Leu Ser Asn Asp Asn
                485                 490                 495
Glu Phe
```

```
<210> SEQ ID NO 13
<211> LENGTH: 498
<212> TYPE: PRT
<213> ORGANISM: Crotalus atrox

<400> SEQUENCE: 13
```

```
Ala His Asp Arg Asn Pro Leu Glu Glu Cys Phe Arg Glu Thr Asp Tyr
1               5                   10                  15
Glu Glu Phe Leu Glu Ile Ala Lys Asn Gly Leu Thr Ala Thr Ser Asn
                20                  25                  30
Pro Lys Arg Val Val Ile Gly Ala Gly Met Ala Gly Leu Ser Ala
            35                  40                  45
Ala Tyr Val Leu Ala Gly Ala Gly His Gln Val Thr Val Leu Glu Ala
        50                  55                  60
Ser Glu Arg Val Gly Gly Arg Val Arg Thr Tyr Arg Lys Lys Asp Trp
65                  70                  75                  80
```

```
Tyr Ala Asn Leu Gly Pro Met Arg Leu Pro Thr Lys His Arg Ile Val
                85                  90                  95

Arg Glu Tyr Ile Lys Lys Phe Asp Leu Lys Leu Asn Glu Phe Ser Gln
            100                 105                 110

Glu Asn Glu Asn Ala Trp Tyr Phe Ile Lys Asn Ile Arg Lys Arg Val
        115                 120                 125

Arg Glu Val Lys Asn Asn Pro Gly Leu Leu Glu Tyr Pro Val Lys Pro
    130                 135                 140

Ser Glu Glu Gly Lys Ser Ala Ala Gln Leu Tyr Val Glu Ser Leu Arg
145                 150                 155                 160

Lys Val Val Glu Glu Leu Arg Ser Thr Asn Cys Lys Tyr Ile Leu Asp
                165                 170                 175

Lys Tyr Asp Thr Tyr Ser Thr Lys Glu Tyr Leu Leu Lys Glu Gly Asn
            180                 185                 190

Leu Ser Pro Gly Ala Val Asp Met Ile Gly Asp Leu Leu Asn Glu Asp
        195                 200                 205

Ser Gly Tyr Tyr Val Ser Phe Ile Glu Ser Leu Lys His Asp Asp Ile
    210                 215                 220

Phe Gly Tyr Glu Lys Arg Phe Asp Glu Ile Val Gly Gly Met Asp Gln
225                 230                 235                 240

Leu Pro Thr Ser Met Tyr Glu Ala Ile Lys Glu Lys Val Gln Val His
                245                 250                 255

Phe Asn Ala Arg Val Ile Glu Ile Gln Gln Asn Asp Arg Glu Ala Thr
            260                 265                 270

Val Thr Tyr Gln Thr Ser Ala Asn Glu Met Ser Ser Val Thr Ala Asp
        275                 280                 285

Tyr Val Ile Val Cys Thr Thr Ser Arg Ala Ala Arg Arg Ile Lys Phe
    290                 295                 300

Glu Pro Pro Leu Pro Pro Lys Lys Ala His Ala Leu Arg Ser Val His
305                 310                 315                 320

Tyr Arg Ser Gly Thr Lys Ile Phe Leu Thr Cys Thr Lys Lys Phe Trp
                325                 330                 335

Glu Asp Asp Gly Ile His Gly Gly Lys Ser Thr Thr Asp Leu Pro Ser
            340                 345                 350

Arg Phe Ile Tyr Tyr Pro Asn His Asn Phe Thr Ser Gly Val Gly Val
        355                 360                 365

Ile Ile Ala Tyr Gly Ile Gly Asp Asp Ala Asn Phe Phe Gln Ala Leu
    370                 375                 380

Asp Phe Lys Asp Cys Ala Asp Ile Val Ile Asn Asp Leu Ser Leu Ile
385                 390                 395                 400

His Glu Leu Pro Lys Glu Asp Ile Gln Thr Phe Cys His Pro Ser Met
                405                 410                 415

Ile Gln Arg Trp Ser Leu Asp Lys Tyr Ala Met Gly Gly Ile Thr Thr
            420                 425                 430

Phe Thr Pro Tyr Gln Phe Gln His Phe Ser Glu Ala Leu Thr Ala Pro
        435                 440                 445

Phe Lys Arg Ile Tyr Phe Ala Gly Glu Tyr Thr Ala Gln Phe His Gly
    450                 455                 460

Trp Ile Asp Ser Thr Ile Lys Ser Gly Leu Thr Ala Ala Arg Asp Val
465                 470                 475                 480

Asn Arg Ala Ser Glu Asn Pro Ser Gly Ile His Leu Ser Asn Asp Asn
                485                 490                 495
```

Glu Phe

<210> SEQ ID NO 14
<211> LENGTH: 618
<212> TYPE: PRT
<213> ORGANISM: Trichoderma viride

<400> SEQUENCE: 14

Met Asp Asn Val Asp Phe Ala Glu Ser Val Arg Thr Arg Trp Ala Arg
1               5                   10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Arg Glu Gly Arg Phe
        35                  40                  45

Leu Gly Gly Gly Tyr Ser His Asp Asn Leu Pro Ser Asp Pro Leu Tyr
    50                  55                  60

Ser Ser Ile Lys Pro Ala Leu Leu Lys Glu Ala Pro Arg Ala Glu Glu
65                  70                  75                  80

Glu Leu Pro Pro Arg Lys Val Cys Ile Val Gly Ala Gly Val Ser Gly
                85                  90                  95

Leu Tyr Ile Ala Met Ile Leu Asp Asp Leu Lys Ile Pro Asn Leu Thr
            100                 105                 110

Tyr Asp Ile Phe Glu Ser Ser Ser Arg Thr Gly Gly Arg Leu Tyr Thr
        115                 120                 125

His His Phe Thr Asp Ala Lys His Asp Tyr Tyr Asp Ile Gly Ala Met
130                 135                 140

Arg Tyr Pro Asp Ile Pro Ser Met Lys Arg Thr Phe Asn Leu Phe Lys
145                 150                 155                 160

Arg Thr Gly Met Pro Leu Ile Lys Tyr Tyr Leu Asp Gly Glu Asn Thr
                165                 170                 175

Pro Gln Leu Tyr Asn Asn His Phe Phe Ala Lys Gly Val Val Asp Pro
            180                 185                 190

Tyr Met Val Ser Val Ala Asn Gly Gly Thr Val Pro Asp Asp Val Val
        195                 200                 205

Asp Ser Val Gly Glu Lys Leu Gln Gln Ala Phe Gly Tyr Tyr Lys Glu
    210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
        275                 280                 285

Asp Ser Phe Asp Phe Asp Asn Pro Thr Lys Pro Glu Trp Tyr Cys Ile
    290                 295                 300

Glu Gly Gly Thr Ser Leu Leu Val Asp Ala Met Lys Glu Thr Leu Val
305                 310                 315                 320

His Lys Val Gln Asn Asn Lys Arg Val Glu Ala Ile Ser Ile Asp Leu
                325                 330                 335

Asp Ala Pro Asp Asp Gly Asn Met Ser Val Lys Ile Gly Gly Lys Asp
            340                 345                 350

Tyr Ser Gly Tyr Ser Thr Val Phe Asn Thr Thr Ala Leu Gly Cys Leu
        355                 360                 365

-continued

```
Asp Arg Met Asp Leu Arg Gly Leu Asn Leu His Pro Thr Gln Ala Asp
    370                 375                 380
Ala Ile Arg Cys Leu His Tyr Asp Asn Ser Thr Lys Val Ala Leu Lys
385                 390                 395                 400
Phe Ser Tyr Pro Trp Trp Ile Lys Asp Cys Gly Ile Thr Cys Gly Gly
                405                 410                 415
Ala Ala Ser Thr Asp Leu Pro Leu Arg Thr Cys Val Tyr Pro Ser Tyr
                420                 425                 430
Asn Leu Gly Asp Thr Gly Glu Ala Val Leu Leu Ala Ser Tyr Thr Trp
            435                 440                 445
Ser Gln Asp Ala Thr Arg Ile Gly Ser Leu Val Lys Asp Ala Pro Pro
    450                 455                 460
Gln Pro Pro Lys Glu Asp Glu Leu Val Glu Leu Ile Leu Gln Asn Leu
465                 470                 475                 480
Ala Arg Leu His Ala Glu His Met Thr Tyr Glu Lys Ile Lys Glu Ala
                485                 490                 495
Tyr Thr Gly Val Tyr His Ala Tyr Cys Trp Ala Asn Asp Pro Asn Val
                500                 505                 510
Gly Gly Ala Phe Ala Leu Phe Gly Pro Gly Gln Phe Ser Asn Leu Tyr
            515                 520                 525
Pro Tyr Leu Met Arg Pro Ala Ala Gly Gly Lys Phe His Ile Val Gly
    530                 535                 540
Glu Ala Ser Ser Val His His Ala Trp Ile Ile Gly Ser Leu Glu Ser
545                 550                 555                 560
Ala Tyr Thr Ala Val Tyr Gln Phe Leu Tyr Lys Tyr Lys Met Trp Asp
                565                 570                 575
Tyr Leu Arg Leu Leu Leu Glu Arg Trp Gln Tyr Gly Leu Gln Glu Leu
            580                 585                 590
Glu Thr Gly Lys His Gly Thr Ala His Leu Gln Phe Ile Leu Gly Ser
            595                 600                 605
Leu Pro Lys Glu Tyr Gln Val Lys Ile Val
    610                 615
```